(12) United States Patent
Brown et al.

(10) Patent No.: US 11,432,873 B2
(45) Date of Patent: *Sep. 6, 2022

(54) METHODS AND DEVICES FOR ACCESS ACROSS ADJACENT TISSUE LAYERS

(71) Applicant: Boston Scientific Scimed, Inc., Maple Grove, MN (US)

(72) Inventors: Peter Brown, Palo Alto, CA (US); Sith Khoune, Fremont, CA (US); Keke Lepulu, Menlo Park, CA (US); Ryan Donovan, Santa Clara, CA (US); Kenneth F. Binmoeller, San Francisco, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/919,883

(22) Filed: Jul. 2, 2020

(65) Prior Publication Data

US 2020/0330156 A1 Oct. 22, 2020

Related U.S. Application Data

(63) Continuation of application No. 15/147,731, filed on May 5, 2016, now Pat. No. 10,729,492, which is a
(Continued)

(51) Int. Cl.
*A61B 18/14* (2006.01)
*A61B 17/34* (2006.01)
(Continued)

(52) U.S. Cl.
CPC ...... *A61B 18/1492* (2013.01); *A61B 17/1114* (2013.01); *A61B 17/320016* (2013.01);
(Continued)

(58) Field of Classification Search
CPC ............ A61B 18/1492; A61B 18/1402; A61B 2018/1425; A61B 2018/144;
(Continued)

(56) References Cited

U.S. PATENT DOCUMENTS 10,729,492 B2 * 8/2020 Brown ................ A61B 17/1114
2002/0111620 A1 * 8/2002 Cooper .............. A61B 18/1485
606/41
(Continued)

FOREIGN PATENT DOCUMENTS

JP 2012521267 A 9/2012
JP 6342431 B2 6/2018

OTHER PUBLICATIONS

Binmoeller et al., "A novel lumen-apposing stent for transluminal drainage of nonadherent extraintestinal fluid collections", Endoscopy 43(4): 337-42 (2011).
(Continued)

*Primary Examiner* — Thomas A Giuliani
(74) *Attorney, Agent, or Firm* — Seager, Tufte & Wickhem, LLP

(57) ABSTRACT

Adjacent tissue layers can be accessed using a catheter device with a distal tip having a conductive portion including a first cutting feature and one or more projections extending from the first cutting feature towards an outer diameter of the distal tip. Electrical energy can be supplied to the conductive portion of the device to cut tissue. A stent can be delivered to form a fluid communication between the adjacent tissue layers.

19 Claims, 28 Drawing Sheets

Related U.S. Application Data continuation of application No. 13/871,978, filed on Apr. 26, 2013, now Pat. No. 9,381,041.

(60) Provisional application No. 61/767,577, filed on Feb. 21, 2013, provisional application No. 61/727,629, filed on Nov. 16, 2012, provisional application No. 61/648,544, filed on May 17, 2012.

(51) Int. Cl.
*A61B 18/12* (2006.01)
*A61B 17/11* (2006.01)
*A61B 17/32* (2006.01)
*A61B 18/00* (2006.01)
*A61B 17/00* (2006.01)

(52) U.S. Cl.
CPC ...... *A61B 17/3476* (2013.01); *A61B 17/3478* (2013.01); *A61B 18/1206* (2013.01); *A61B 2017/00278* (2013.01); *A61B 2017/346* (2013.01); *A61B 2017/3425* (2013.01); *A61B 2017/3454* (2013.01); *A61B 2018/00345* (2013.01); *A61B 2018/00494* (2013.01); *A61B 2018/00601* (2013.01); *A61B 2018/144* (2013.01); *A61B 2018/1407* (2013.01); *A61B 2018/1412* (2013.01); *A61B 2018/1425* (2013.01)

(58) Field of Classification Search
CPC .. A61B 2018/1412; A61B 2018/00273; A61B 2018/00279; A61B 2018/00345; A61B 2018/00601; A61B 2018/00494; A61B 17/1114; A61B 17/320016; A61B 17/3478; A61B 2017/3425; A61B 2017/346; A61B 2017/3454; A61B 2017/00278
USPC .... 606/41, 43–46, 49; 607/98, 99, 113, 115, 607/116
See application file for complete search history.

(56) References Cited

U.S. PATENT DOCUMENTS

| | | |
|---|---|---|
| 2004/0167514 A1 | 8/2004 | Okada |
| 2006/0111704 A1* | 5/2006 | Brenneman ............ A61B 17/11 606/41 |
| 2008/0077130 A1 | 3/2008 | Shibata et al. |
| 2009/0143713 A1 | 6/2009 | Van Dam et al. |
| 2009/0270888 A1 | 10/2009 | Patel et al. |

OTHER PUBLICATIONS

Binmoeller et al., "Endoscopic ultrasound-guided gastroenterostomy using novel tools designed for transluminal therapy: a porcine study" Endoscopy 2012; 44: 499-503.

* cited by examiner

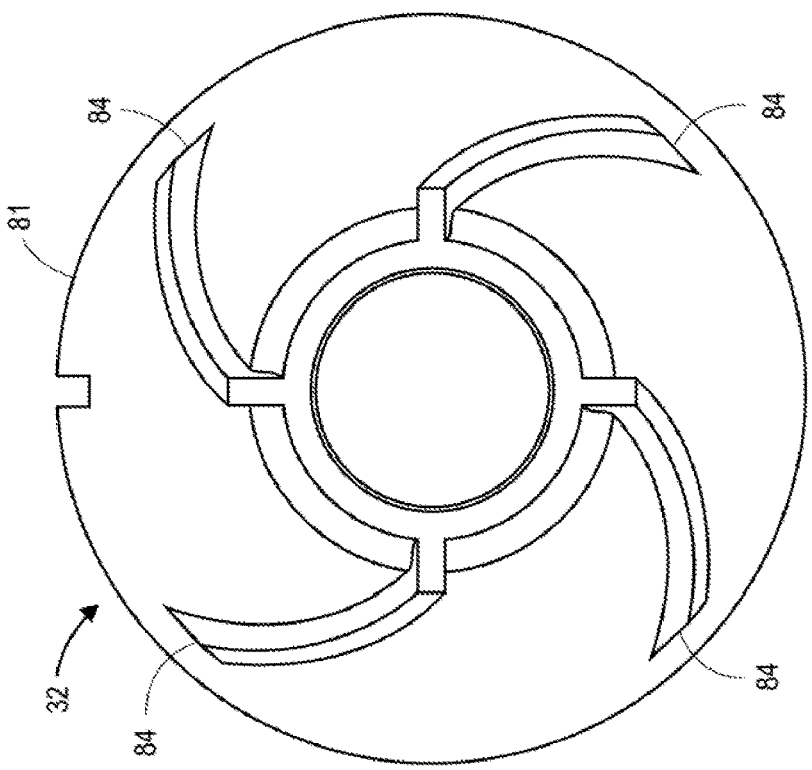
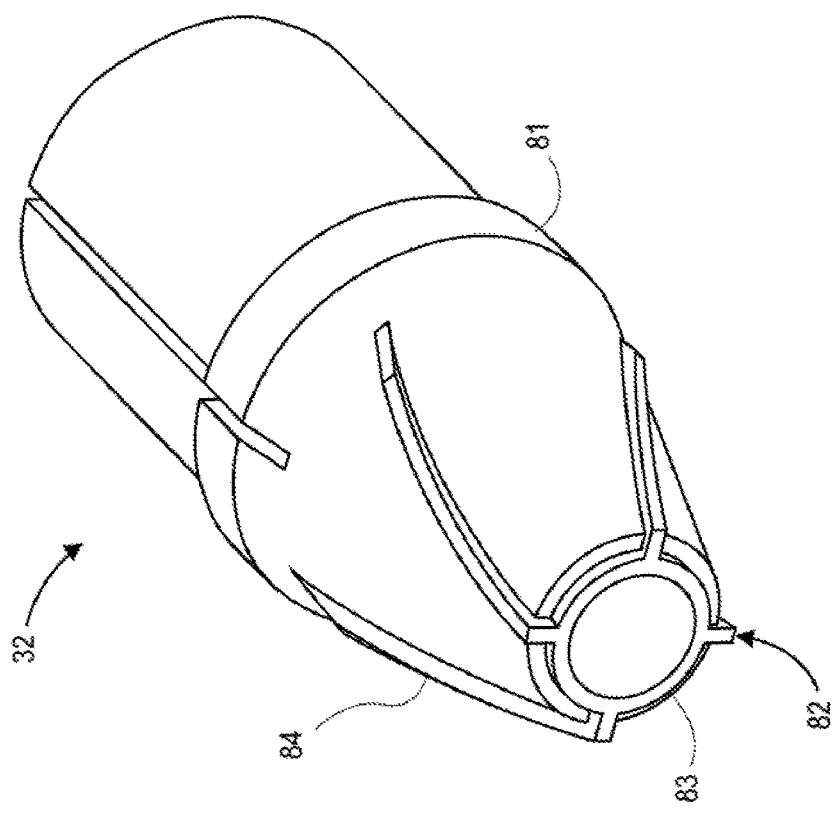
FIG. 8B
FIG. 8A

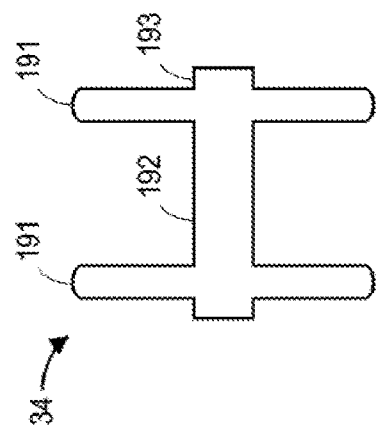
FIG. 18C
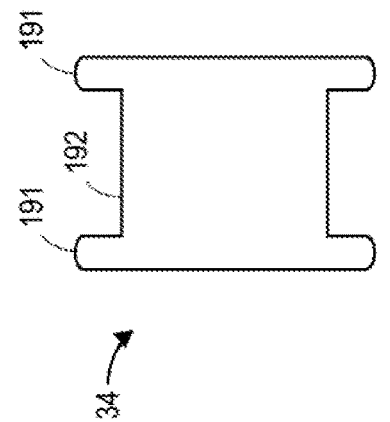
FIG. 18F
FIG. 18B
FIG. 18E
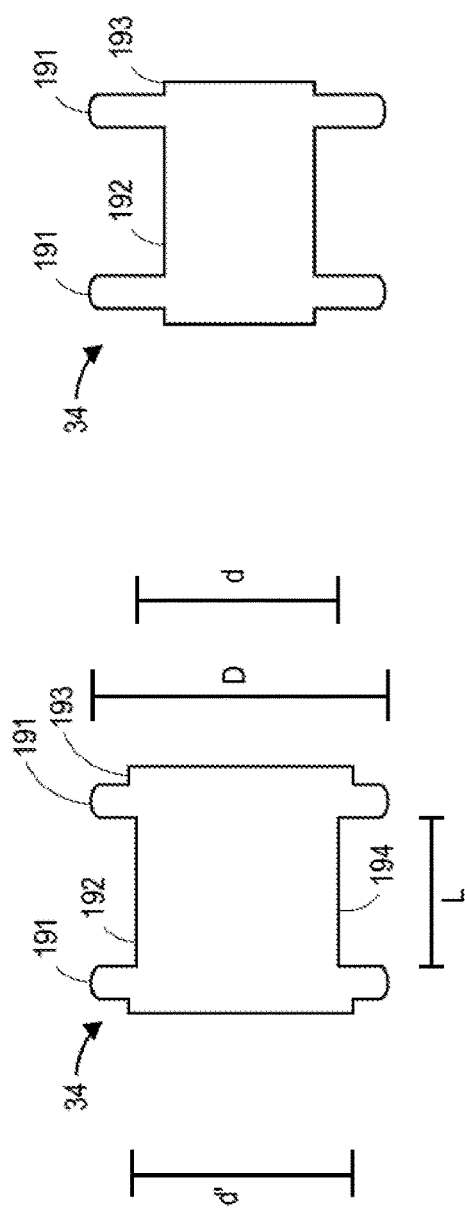
FIG. 18A
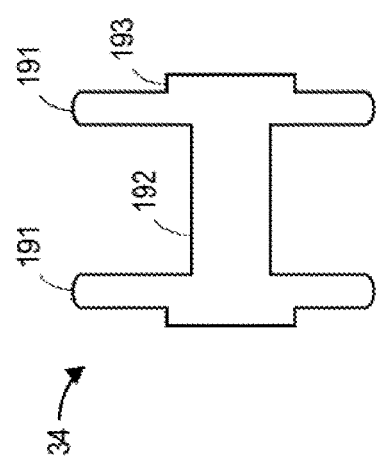
FIG. 18D

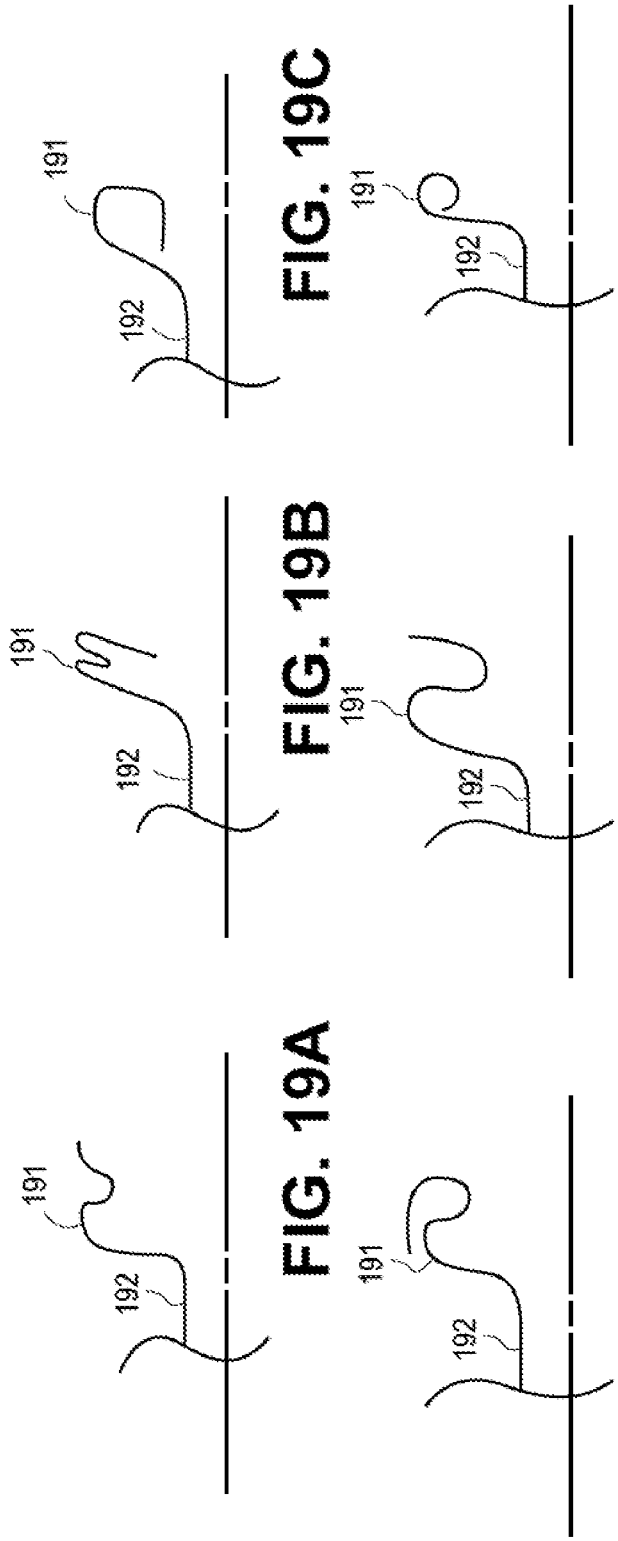

METHODS AND DEVICES FOR ACCESS ACROSS ADJACENT TISSUE LAYERS

CROSS REFERENCE TO RELATED APPLICATIONS

This application is a continuation of U.S. patent application Ser. No. 15/147,731, filed May 5, 2016, now granted as U.S. Pat. No. 10,729,492, which is a continuation of U.S. patent application Ser. No. 13/871,978, filed Apr. 26, 2013, now granted as U.S. Pat. No. 9,381,041, which claims priority to U.S. Provisional Application No. 61/648,544, filed May 17, 2012, U.S. Provisional Application No. 61/727,629, filed Nov. 16, 2012, and U.S. Provisional Application No. 61/767,577, filed Feb. 21, 2013, the disclosure of each of which is incorporated by reference herein in its entirety.

This application is related to U.S. patent application Ser. No. 13/281,410, filed Oct. 25, 2011, U.S. patent application Ser. No. 13/363,297, filed Jan. 31, 2012, U.S. patent application Ser. No. 12/772,762, filed May 3, 2010, U.S. patent application Ser. No. 12/790,553, filed May 28, 2010, U.S. patent application Ser. No. 12/427,254, filed Apr. 21, 2009, and U.S. patent application Ser. No. 12/427,215, filed Apr. 21, 2009, the disclosures of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates generally to medical methods and apparatus. More particularly, the present disclosure relates to methods and apparatus for penetrating adjacent tissue layers and enlarging the resulting penetration.

BACKGROUND

A number of inter and intra-luminal endoscopic procedures require precise placement of anchors or stents. For example, a number of procedures may be performed by entering the gastrointestinal (GI) tract through a first organ or structure, such as the esophagus, stomach, duodenum, small intestine, or large intestine, and delivering the anchor or stent to adjacent organs and lumen or tissue structures such as an adjacent portion of the GI tract, the bile duct, the pancreatic duct, the gallbladder, the pancreas, cysts, pseudocysts, abscesses, and the like. While primarily intended for use in the GI tract, such methods and apparatus can also be used for access to and from portions of the urinary tract, such as the urinary bladder and ureter, the pulmonary tract, such as the trachea and bronchi, and the biliary tract, such as the bile duct and gallbladder, as well.

Intra-ductal stents are commonly used to facilitate the opening of closed vessels for access, drainage or other purposes. Tissue anchors are used to secure adjacent tissues or organs. Inter-luminal tissue anchors, which include a central lumen, are used to facilitate fluid communication between adjacent ducts, organs or lumens. Often, the precise placement of the tissue anchor or stent is necessary, especially when the tissue anchor or stent has well defined anchoring elements at the proximal and/or distal ends, and the device is used to secure adjacent lumens.

When deploying a stent or other tissue anchor between adjacent body lumens, organs, or other structures, it is typically necessary to penetrate both a wall of the first body lumen through which access is established and a wall of a second body lumen which is the target for the procedure. When initially forming such access penetrations, there is a significant risk of leakage from either or both of the access body lumen and the target body lumen into the surrounding space including, but not limited to the peritoneal cavity. In some procedures, such as those involving transgastric or transduodenal bile duct access, loss of body fluid into surrounding tissues and body cavities can present a substantial risk to the patient. The risk can be exacerbated when it is necessary to not only penetrate the luminal walls to gain initial access, usually with a needle, but to subsequently enlarge or dilate the initial penetration, for example by passing a tapered dilator over the needle used to establish initial access. Dilation of the initial tissue penetration can cause additional damage to the tissue penetration and is an additional opportunity for leakage.

Thus, it would be desirable to establish initial luminal wall penetrations and to subsequently dilate said penetrations in order to deploy a stent, anchor, or for other purposes, while minimizing the risk of body fluid leakage. It is also desirable for improved access to body lumens while minimizing trauma and damage to the tissue surrounding the initial luminal wall penetration. It would be further desirable to provide improved protocols and access tools which are capable of being deployed from endoscopes present in a first body lumen to access adjacent body lumens or cavities while minimizing the risk of leakage. Such access tools and protocols should be compatible with a wide variety of procedures, such as placement of stents or other tissue anchors between adjacent luminal walls, and will preferably reduce or eliminate the need to exchange tools during the access procedure.

SUMMARY OF THE DISCLOSURE

Methods for advancing a catheter distally through opposed first and second luminal walls of first and second body lumens are disclosed herein. The methods include positioning a catheter with a distal tip proximal to the first luminal wall, the catheter including a stent; providing an electrical current to a conductive portion of the distal tip; advancing distally the distal tip of the catheter through the first and second luminal walls to create a passage therethrough, wherein the conductive portion of the distal tip includes a first cutting feature and one or more projections extending from the first cutting feature towards an outer diameter of the distal tip; deploying a distal flange of the stent in the second body lumen; and drawing proximally on the distal flange to pull the first and second luminal walls towards each other.

The methods can include releasing a proximal flange of the stent into the first body lumen. The methods can include attaching the catheter to an endoscope prior to positioning the catheter.

The methods can also include forming a hole in the first and second body lumens using a needle prior to positioning the catheter. In some embodiments the catheter can be positioned using a guidewire. In some embodiments a guidewire is not used for positioning the catheter and the distal tip does not have a guidewire lumen.

In some embodiments the first cutting feature and one or more projections can have an arced configuration. In some embodiments the first cutting feature comprises a concentric ring that is concentric to a lumen in the distal tip of the catheter. In some embodiments the catheter is disposed about a guidewire and positioning includes advancing the catheter along the guidewire, wherein the concentric ring is configured to be disposed about the guidewire.

In some embodiments the catheter includes a sheath radially constraining the stent, the stent being a self-expanding stent. Deploying the proximal and distal flanges can include retracting the sheath to allow the proximal and distal flanges of the stent to expand. In some embodiments the methods include verifying the deployment of the distal flange prior to drawing proximally. Verifying the deployment of the distal flange can be done using ultrasound.

In some embodiments advancing the distal tip through the first and second luminal walls to create the passage therethrough forms a first patterned hole in the first luminal wall and a second patterned hole in the second luminal wall. The first and second patterned holes can have a diameter that is less than the maximum diameter of the distal tip. The first and second patterned holes can each include a central hole with one or more projections radiating from the central hole.

The first body lumen can be within the digestive tract. In some embodiments the first body lumen is selected from the group consisting of: esophagus, stomach, duodenum, jejunum, small intestine, large intestine, colon, and rectum. The second body lumen can be part of the digestive tract or biliary tree. In some embodiments the second body lumen is selected from the group consisting of: esophagus, stomach, duodenum, jejunum, small intestine, large intestine, colon, bile duct, pancreatic duct, gallbladder, and pancreas. In some embodiments the first and second body lumens are sections of the colon. In some embodiments the first body lumen is the stomach or duodenum and the second body lumen is the gallbladder. In some embodiments the first and second body lumens are a fundal pouch and a section of the duodenum or jejunum.

The methods can include forming an anastomosis between the first and second body lumens. The methods can include removing the stent after forming the anastomosis.

Catheter assemblies are disclosed herein. The catheter assemblies can include a catheter body having a proximal end, a distal end, and a central passage therethrough; and a tip positioned near the distal end of the catheter body, the tip having a conductive portion including a first cutting feature and one or more projections outwardly extending from the first cutting feature towards an outer diameter of the tip, the conductive portion configured to be electrically coupled to an electrosurgical generator.

In some embodiments the first cutting feature and one or more projections has an arced configuration. In some embodiments the first cutting feature comprises a concentric ring. In some embodiments the catheter has a guidewire lumen and the concentric ring is configured to be disposed about and insulated from the guidewire lumen. In some embodiments the tip does not have a guidewire lumen.

In some embodiments the conductive portion including two projections. In some embodiments the conductive portion including four projections. In some embodiments the conductive portion includes an exterior portion made of stainless steel and an interior portion comprising copper electrically coupled to the exterior portion and configured to be electrically coupled to an electrosurgical generator.

In some embodiments the one or more outwardly extending projections extend from the first cutting feature to a maximum radial position, the maximum radial position defining a length between the radial position and a center point of the distal tip, wherein the length is less than 50% of the outer diameter of the tip. In some embodiments the one or more projections outwardly extending from the first cutting feature towards the outer diameter of the tip include a covered portion adjacent to a maximum diameter of the tip.

In some embodiments the catheter includes a compartment within the catheter body configured to hold a stent. A stent can be included within the compartment within the catheter body. The stent can be self-expanding. The self-expanding stent can be radially restrained by a movable sheath. The stent can be configured to expand to form distal and proximal double-walled flanges. In some embodiments the stent can have a pull-out strength of greater than about 400 grams.

The catheter can be configured to be attached to an endoscope. The catheter can also include a control handle configured to control the energy provided by the electrosurgical generator to the first cutting feature and the one or more projections. The electrosurgical generator can be configured to supply about 50 watts to about 100 watts of power to the conductive portion of the tip.

In some embodiments the catheter assembly includes an inner catheter shaft engaged with the distal tip and configured to move relative to the catheter body within the central passage of the catheter body. The inner catheter shaft and distal tip can be configured to be removable from the catheter body.

In some embodiments methods for advancing a catheter distally through a luminal wall of a first body lumen are provided. The methods include positioning a catheter comprising an outer tubular body and inner body with a distal tip proximal to the luminal wall of the first body lumen; providing an electrical current to a conductive portion of the distal tip; advancing distally the distal tip of the catheter through the first luminal wall along with a portion of the outer tubular body to create a passage therethrough, wherein the conductive portion of the distal tip includes a first cutting feature and one or more projections extending from the first cutting feature towards an outer diameter of the distal tip; and withdrawing the inner body and distal tip through the outer tubular body leaving a portion of the outer tubular body in the passage in the luminal wall of the first body lumen. The first luminal wall can be the transgastric wall or transduodenal wall. The methods can include forming a hole in a pseudocyst during advancing distally. The methods can also include passing a catheter, stent, or drainage device through the outer tubular body and into the hole in the pseudocyst.

Positioning can include following a guidewire to a target location of the luminal wall of the first body lumen. The first cutting feature can be a concentric ring that is concentric to a lumen in the distal tip of the catheter. The first cutting feature and one or more projections can be an arced configuration.

In some embodiments the methods include deploying a distal flange of a stent in the pseudocyst and deploying a proximal flange of the stent in contact with the transgastric wall or transduodenal wall.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 8A-8B illustrate various views of a distal tip in accordance with an embodiment.

FIGS. 18A-18F illustrate various configurations of stents that can be delivered using the devices disclosed herein in accordance with embodiments.

FIGS. 19A-19I illustrate various configurations of stents that can be delivered using the devices disclosed herein in accordance with embodiments.

DETAILED DESCRIPTION

Improved catheter tip designs are disclosed herein. The designs disclosed herein offer a number of advantages over prior art designs. The devices disclosed herein can more quickly and efficiently cut through tissue with less leakage, trauma, and thermal damage to surrounding tissue than previous designs. Conventional blunt tip designs require higher power that can cause excessive heating that can also damage tissue adjacent to the target area. The prior art tip designs can also require longer amounts of time to cut the tissue. The longer exposure times can further exacerbate thermal damage to tissue. It is desirable for improved catheter tip designs to overcome many of the problems with the prior art tip designs.

Figure 1:
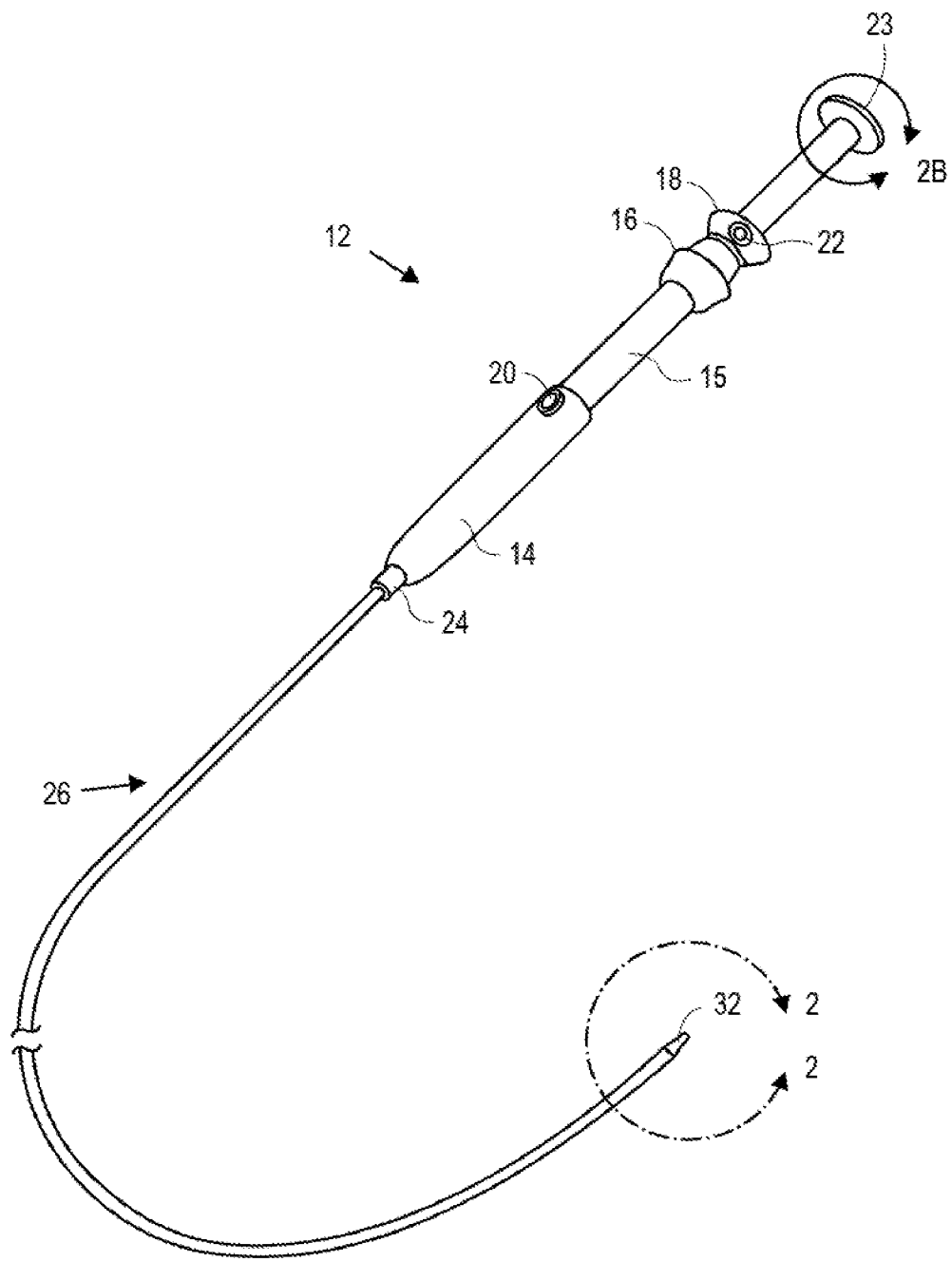
FIG. 1 is a perspective view of a catheter constructed in accordance with the principles of the present disclosure.
Figure 2A:
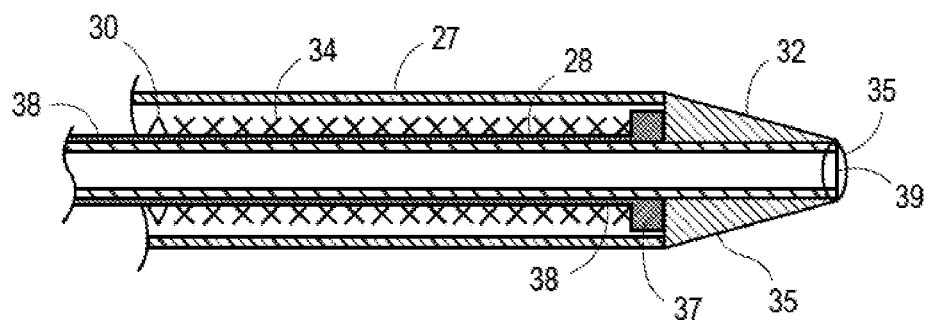
FIG. 2A illustrates one embodiment of a distal tip of the catheter of FIG. 1.
Figure 2B:
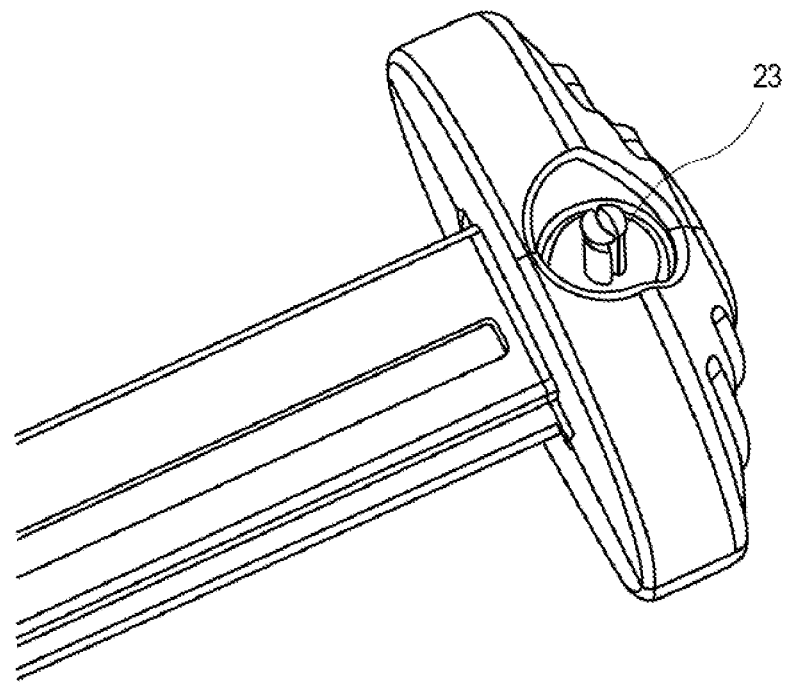
FIG. 2B illustrates one embodiment of a handle of the catheter of FIG. 1.

The device 10 of FIG. 1 includes a control handle 12 having a body 14 with a first slide actuator 15 with knob 16 and lock 20. A second slide actuator 18 with lock 22, scope locking mechanism 24, electrical plug 23, catheter body 26, a sheath 27, shaft 28, stent lock 30, distal tapered tip 32 and stent or other tissue anchor 34 (FIG. 2A). FIG. 2A is an enlarged portion of the end of the device 10, including the distal tapered tip 32. FIG. 2B is an enlarged portion of the handle of the device 10, including the electrical plug 23. An electrical source can be plugged into electrical plug 23 to provide electricity.

The distal tapered tip 32 includes a distal tip base 33. The sheath 27 can contact the distal tapered tip and engage with an outer diameter of the distal tip base 33. The stent lock 30 and/or sheath 27 can radially constrain the stent 34 and prevent the stent 34 from expanding. The distal tapered tip 32 includes a conductive portion with a cutting element 35. The illustrated cutting element 35 has a concentric design about a guidewire lumen 39. The conductive projections 36 extend from the cutting element 35 towards the outer diameter of the distal tip 32. The illustrated projections 36 enter into a recessed portion 41 (FIG. 3B) of the distal tip 32.

The conductive areas of the tip, such as the cutting element 35 and projections 36 can be configured to cut, heat, and/or cauterize tissue in a patient. Electrical energy is supplied to energize the conductive areas of the tip. Electrical energy can be supplied to the conductive portions of the tip, such as radiofrequency (RF) and high-frequency (HF) energy. The electrical energy can be supplied through electrical plug 23. The handle includes an electrical control to control the electrical energy supplied to the tip.

The cutting element 35 and illustrated projections 36 can be made out of a conductive medical grade material that is biocompatible, such as stainless steel. A different conductive material, such as copper, can be used to supply electrical energy to the cutting element 35 and projections 36. The projections 36 can connect to the wiring 38 at connection 37. The wiring 38 is in electrical contact with the electrical plug 23. The electrical plug 23 supplies electrical energy through the wiring 38 to the cutting element 35 and projections 36. The distal tip 32 is made out of an insulating material to insulate the cutting element 35 and projections 36 from the surrounding device structure.

Figure 3A:
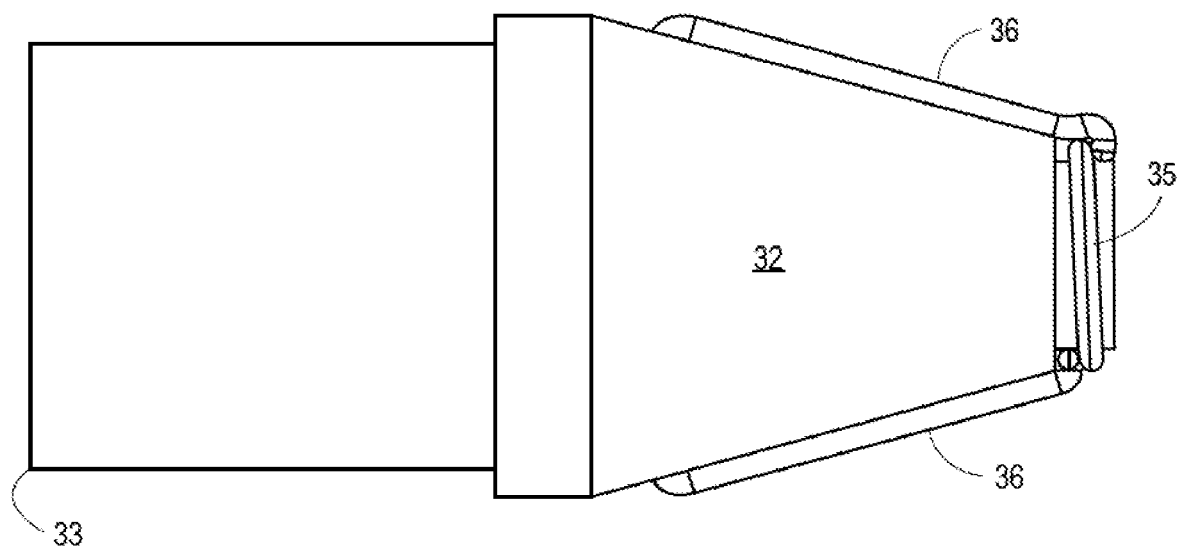
FIGS. 3A-3C illustrate various views of a distal tip of a catheter in accordance with an embodiment.
Figure 3B:
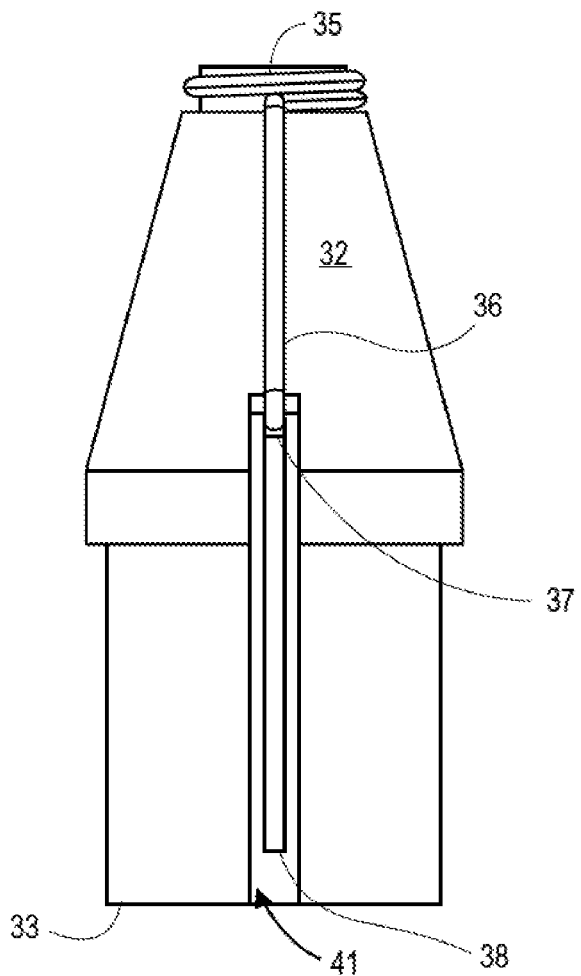
Figure 3C:
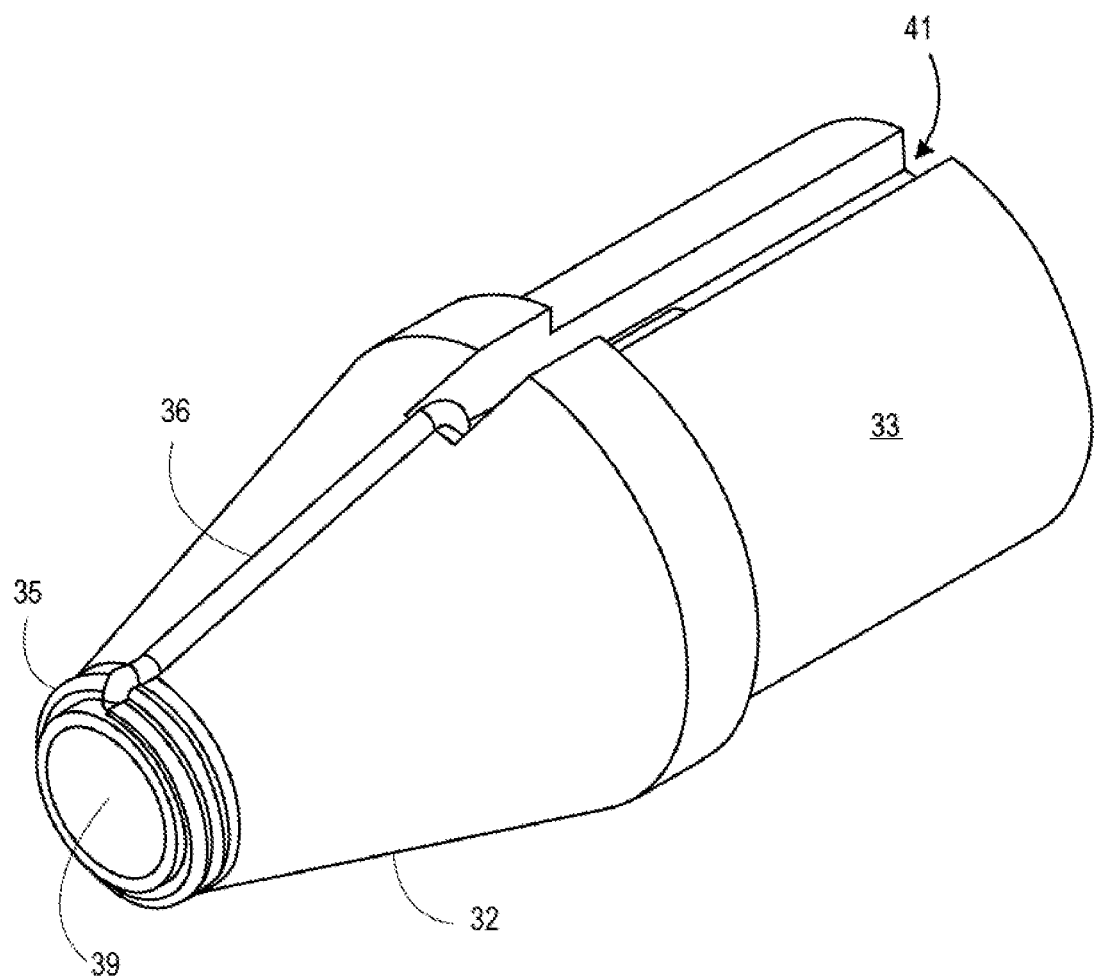
Figure 4B:
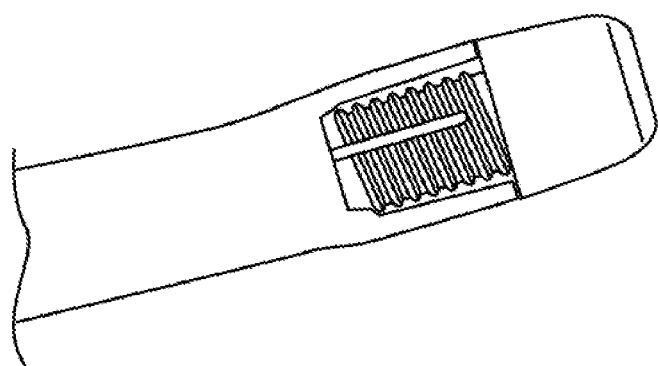
FIG. 4B is an image of a prior art catheter tip.
Figure 4A:
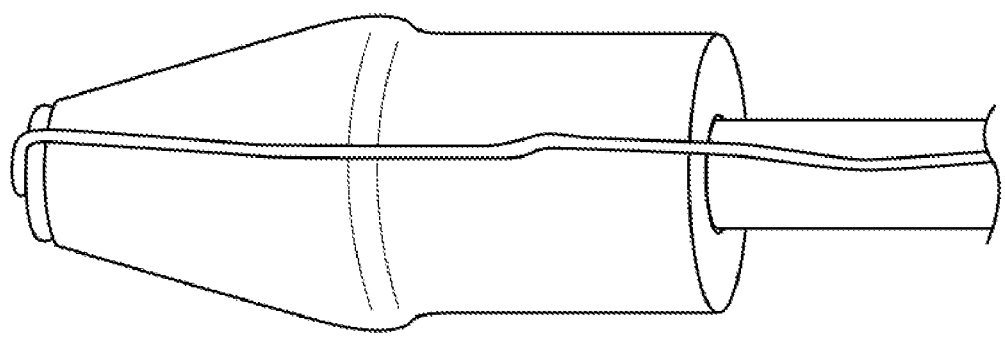
FIG. 4A is an image of a distal tip of a catheter in accordance with an embodiment.

FIGS. 3A-3C illustrate enlarged views of the distal tip 32. FIG. 3A is a side view showing the projections 36 entering the distal tip 32 just short of the outer diameter of the distal tip 32. FIG. 3B is a top view of the distal tip 32 showing the projections 36 entering into the recessed portion 41 of the distal tip 32. FIG. 3C is an isometric view of the distal tip 32. FIG. 4A is an image of the distal tip illustrated in FIGS. 3A-3C.

Figure 16A:
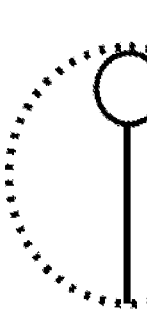
FIGS. 16A-16H illustrate various tissue access patterns made by the devices disclosed herein.
Figure 16B:
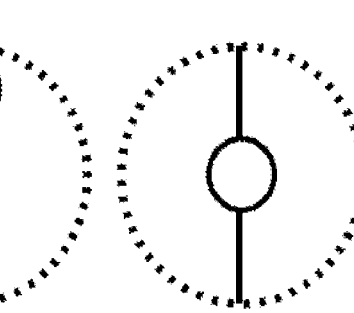
Figure 17:
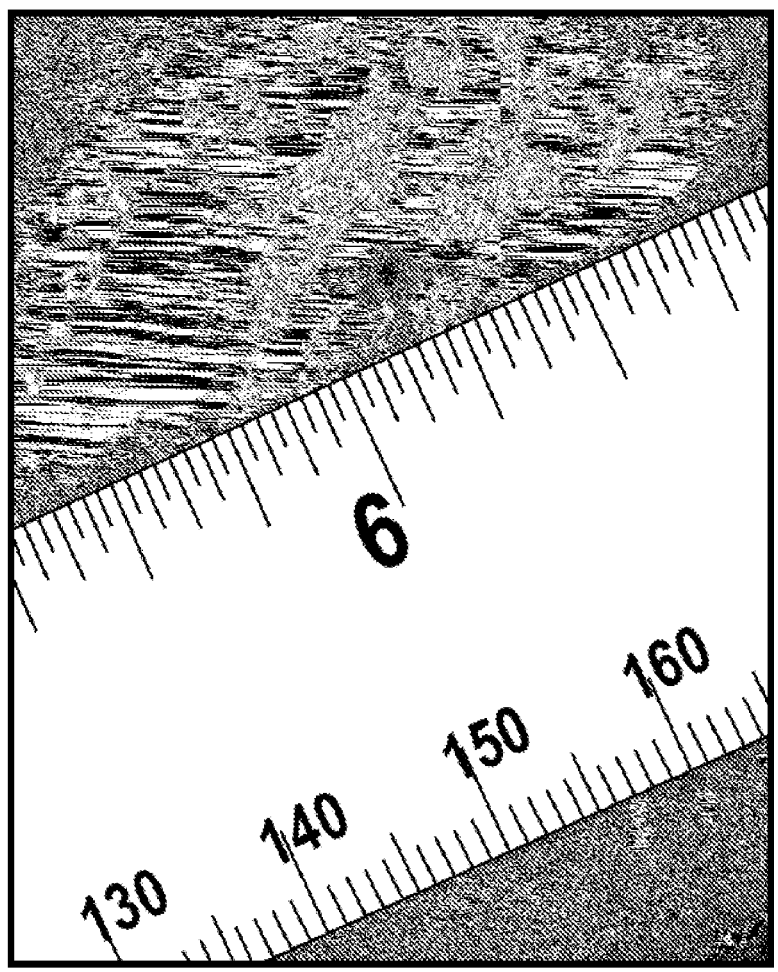
FIG. 17 is an image of a tissue access pattern made using the tip illustrated in FIGS. 3A-3C.

The distal tip shown in FIGS. 3A-3C can produce a tissue cut pattern that contains a central cut region with two linear cuts protruding radially from the central region or ring as shown in FIG. 16B and FIG. 17. The projections 36 in FIGS. 3A-3C recede into the recessed portion 41 of the distal tip 32 before the distal tip 32 reaches its maximum diameter. In some embodiments the projections can be covered adjacent to the outer diameter such that the exposed portion of the projections do not reach the maximum outer diameter of the distal tip 32. The slits made in the tissue by the projections 36 are slightly shorter than the diameter of the tip. Some force can be applied to push the distal tip through the tissue slits made by the energized tip. The elasticity of the tissue can accommodate the slightly larger diameter of the distal tip and catheter. The tight fit can prevent leakage of biological material from the body lumen.

The outwardly extending projections can extend from the first cutting feature to a maximum radial position. The maximum radial position of a projection defines a length between the maximum radial position and the center point of the distal tip. The length between the maximum radial position and center of the tip is less than 50% of the outer diameter of the tip (e.g. two times the length between the maximum radial position and center of the tip is less than 100% of the outer diameter of the tip). In some embodiments the length between the maximum radial position and center of the tip is less than about 47.5% of the outer diameter of the tip. In some embodiments the length between the maximum radial position and center of the tip is less than about 45% of the outer diameter of the tip (e.g. less than about 90% of the outer radius of the tip). In some embodiments the length between the maximum radial position and center of the tip is less than about 40% of the outer diameter of the tip (e.g. less than about 80% of the outer radius of the tip). In some embodiments the length between the maximum radial position and center of the tip is less than about 37.5% of the outer diameter of the tip (e.g. less than about 75% of the outer radius of the tip).

FIGS. 1, 2A, 2B, and 3A-3B illustrate a mono-polar tip that receives current from the wire 38 disposed within the catheter body 14. The wire 38 can extend along the length of the catheter body 14 terminating within the handle 12 of FIG. 1. The wiring 38 and conductive areas of the tip can receive electrical energy, such as RF energy, from a generator unit (not shown) electrically coupled to the handle 12 at the electrical plug 23. The electrical plug 23 is illustrated as a mono-polar plug in FIG. 2B. When the tip comprises a mono-polar design, a grounding pad can be used on the patient. In alternative embodiments, the RF tip can comprise a bi-polar design. In some embodiments providing electrical energy to the conductive areas of the tip can be controlled by an activation switch, dial, or other structure on the handle (not shown). In some embodiments providing electrical energy to the conductive areas of the tip can be controlled using an external switch accessory or foot pedal associated with the electrosurgical generator.

The tip designs disclosed herein allow for an increased electrical current density that can facilitate quicker cutting through tissue and reduced trauma to the surrounding tissue areas. The tip designs reduce the likelihood of leakage and complications for the surgical procedures. FIG. 4B shows a conventional blunt nose conical tip with a welded electrical connection produced by Cook Medical Inc. The tip produced by Cook Medical provides electrical power to the entire blunt tip. The tip requires a relatively large amount of power and carries a lower electrical current density. The lower electrical current density requires longer times to cut through tissue, which can produce excessive heating that can cause damage to the surrounding tissue areas and the surrounding catheter parts. The blunt nose can also cause tearing of the tissue, which increases the chances of leakage of biological material.

FIGS. 5A-5E illustrate steps for accessing adjacent boy lumens, such as lumen L1 and lumen L2. The catheter device 10 is attached to an endoscope 40. The distal end of endoscope or echo-endoscope 40 (FIG. 5A-5E) is positioned usually via trans-oral entry adjacent to a target location within the GI tract.

Initial access between lumen L1 and lumen L2 can be done using a 19 gauge needle. For example, a puncture can be made at the desired location using a 19 gauge needle, such as an electrosurgical needle, followed by placement of a guidewire 102 through the needle lumen. In some embodiments a guidewire is not used. In some embodiments the catheter device 10 can be used for initial access to make a puncture between lumen L1 and lumen L2. Electrical energy can be provided to the cutting element 35 and projections 36 to make the initial puncture in lumen L1 and lumen L2.

Figure 5A:
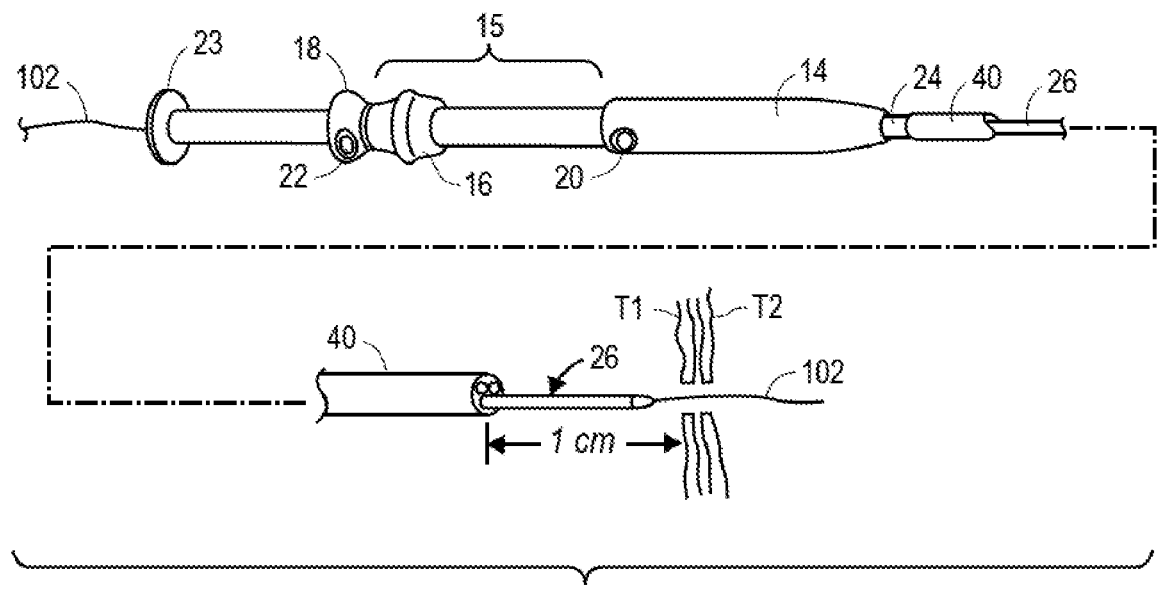
FIGS. 5A-5E illustrate the use of the catheter of FIG. 1 for penetrating opposed luminal walls in accordance with an embodiment.

As illustrated in FIG. 5A, after initial access, the catheter body 26 is advanced over the guidewire 102 through the working channel of the endoscope 40 and is secured to the proximal end of a working channel using scope locking mechanism 24 to locate the catheter body 26 with a tip 32 approximately 1 cm outside of the distal end of the working channel.

Figure 5B:
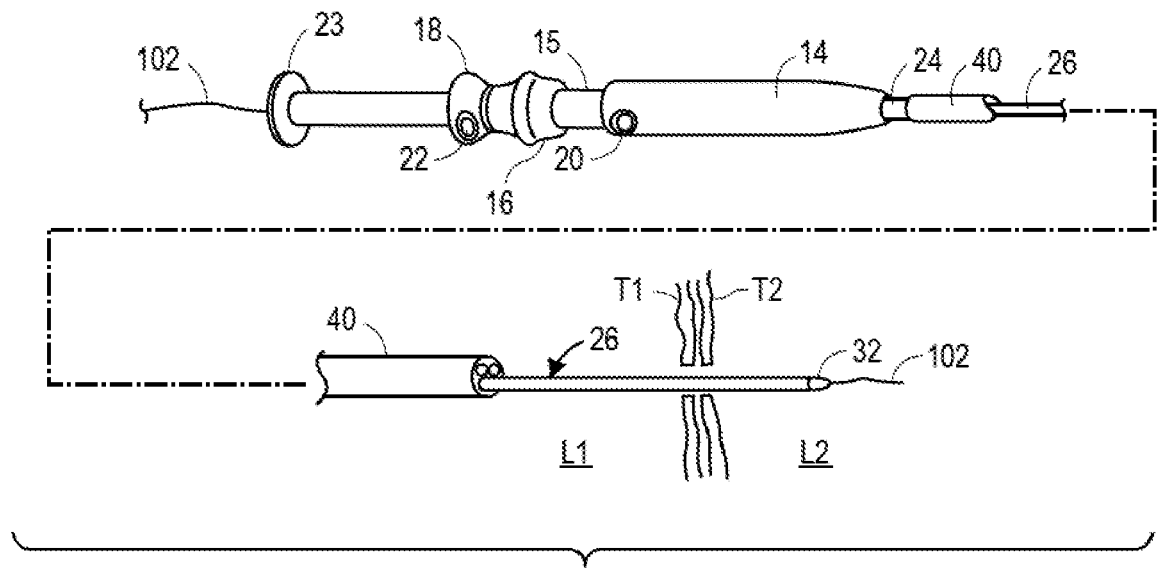
Figure 5C:
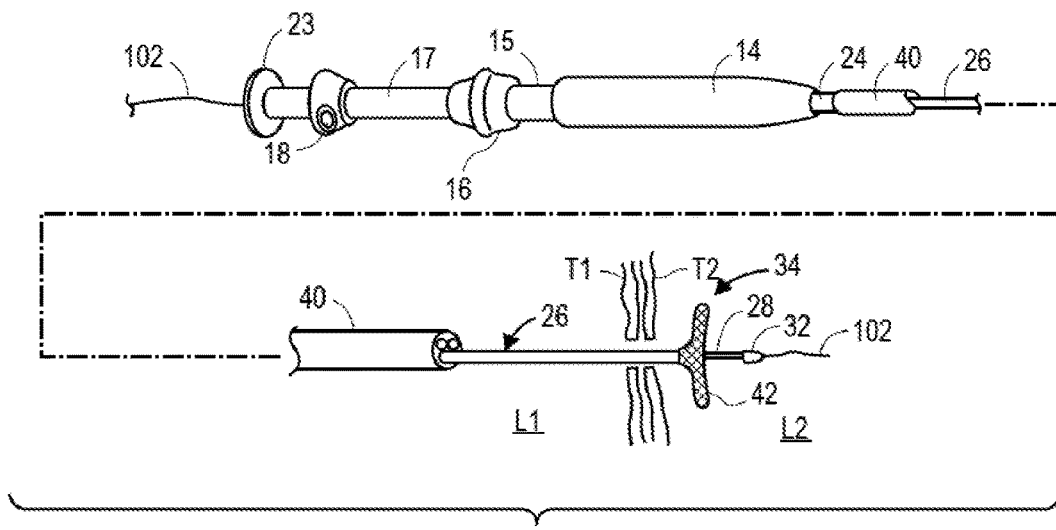

Initial access using a needle typically forms a hole smaller than the diameter of the catheter device 10. The tissue holes in tissue T1 and tissue T2 can be dilated before or during the advancement of the distal tip 32 of the catheter through the penetrations in tissue T1 and tissue T2. Electrical energy can be supplied to the cutting element 35 in order to enlarge the initial penetration in the tissue and facilitate the movement of the catheter shaft through the penetration in tissue T1 and tissue T2. As illustrated in FIG. 5B, the first slide actuator 15 is distally advanced using knob 16, after releasing lock 20, on handle 12, thus moving the assembly of catheter body 26, shaft 28, and stent 34, in the distal direction and through the tract formed through tissue T1 and tissue T2 and moving distal tapered tip 32 from lumen L1 to lumen L2. The electrical plug 23 supplies electrical energy to cutting element 35 and projections 36 to cut the tissue and enlarge the hole. Lock 20 is then reengaged, securing first slide actuator 15 to control handle body 14.

The distal tip 32, cutting element 35, and projections 36 can cut the tissue to enlarge the hole. The tip design illustrated in FIGS. 3A-3C illustrates projections 36 that recede into the inner volume of the distal tip 32 prior to expanding radially to the full diameter of the distal tip 32. The projections 36 cut the tissue T1 and tissue T2 a little bit less than the full diameter of the distal tip 32. The catheter shaft 28 fits snugly into the enlarged holes in tissue T1 and tissue T2 and stretches the openings in tissue T1 and tissue T2 to conform to the diameter of the shaft 28. This forms a tight seal between the catheter shaft 28 and the holes in tissue T1 and tissue T2 thereby limiting the leakage of material enclosed in lumen L1 and lumen L2.

A distal flange segment 42 of the tissue stent or anchor 34 is now expanded by moving the second slide actuator 18 in the proximal direction to retract sheath 27. The second slide actuator is pulled back to a predetermined position part way along the proximal extension 17 of the first slide actuator 15, after releasing second lock 22 as in FIG. 5C. A portion of lock 22 (FIG. 1) of second slide actuator 18 moves in a track (not shown), where said lock 22 engages a stop at a predetermined position, thereby stopping the proximal movement of actuator 18. The predetermined position can be calibrated to allow only the distal flange 42 of tissue anchor 34 to be released from constraint by sheath 27 and to expand. Said proximal motion of second slide actuator 18 retracts the sheath 27, while the shaft 28 is held in place, this releasing the distal portion of tissue anchor 34 from constraint. The catheter operator can pause after deploying the distal flange to verify the expansion of the distal flange. In some embodiments ultrasound can be used to visualize the expansion of the distal flange segment 42. In some embodiments direct visualization of the expansion of the distal flange segment 42 is possible. In some embodiments the sheath can have a visible marker that can be visualized after partial retraction of the sheath. The marker on the sheath can be obscured by the tissue walls prior to retraction. After retracting the sheath a distance sufficient to remove the restraint from the distal flange, the marker on the sheath can then be visible. The marker can be visible under ultrasound imaging, direct visualization, or fluoroscopy. In some cases multiple markers can be used on the sheath with different colors or patterns that can be visually differentiated and correspond to retraction of the sheath over various distances.

Figure 5D:
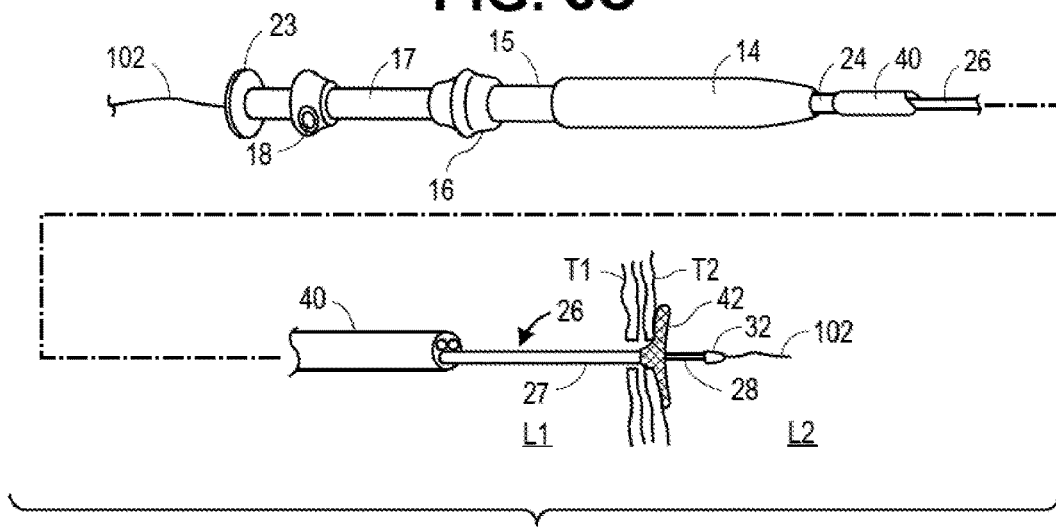

The first slide actuator 15 is now moved slowly in the proximal direction using knob 16, after releasing lock 20, on handle 12, thus moving the expanded distal anchor flange 42 against the inner surface of tissue T2 of lumen L2, and positioning tissue T1 closer to tissue T2, holding lumen L1 and L2 in close apposition as in FIG. 5D. The distal flange 42 can be used to engage and control lumen L2. The distal flange 42 can be used to approximate and adhere lumen L1 and L2.

Stent lock 30 (FIG. 2A) holds the proximal end of the tissue/stent anchor 34 firmly allowing proximal traction against tissue T2. Lock 20 is then reengaged, securing first slide actuator 15 to control handle body 14. The engagement of distal flange 42 with lumen L2 and tissue T2 can be verified prior to releasing the proximal end of the stent 34. The engagement of the distal flange 42 with lumen L2 can be verified using ultrasound or through visualization of a marker on the sheath. The marker on the sheath can be visible once the sheath has been retracted and the distal flange is engaged with tissue T2. For example the marker could be at a distance from the end of the sheath slightly greater than the thickness of the tissue walls T1 and T2. Thus, the marker would only be visible after retracting the sheath to expand the distal flange 42 and engaging the distal flange 42 with tissue T2 thereby making the marker on the sheath visible to the endoscope within lumen L1.

Figure 5E:
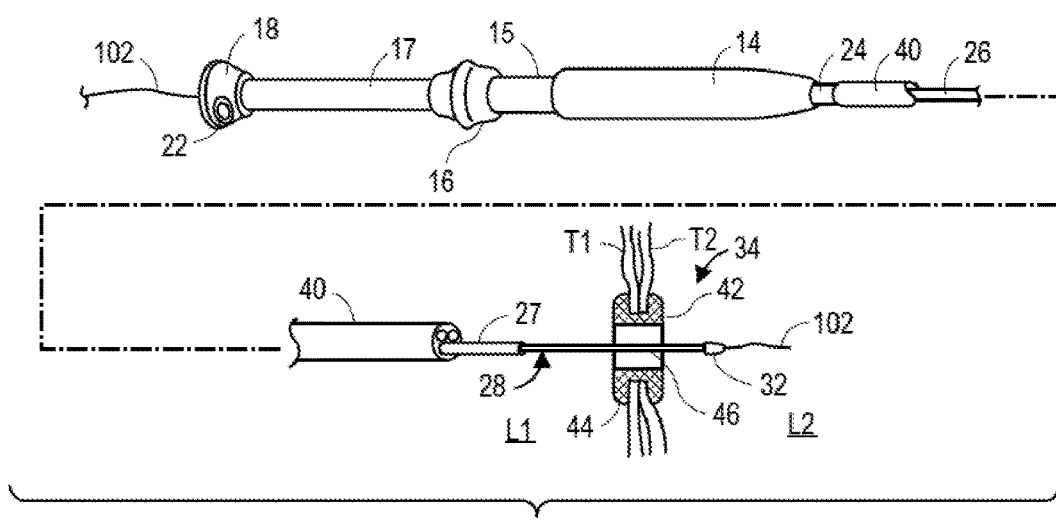
Figure 6A:
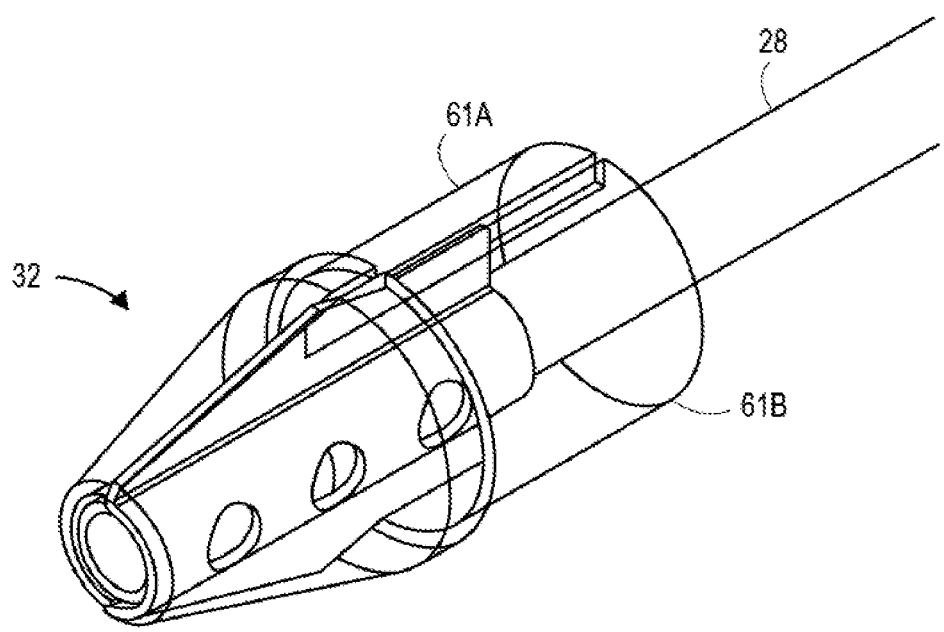
FIGS. 6A-6E illustrate various views of a distal tip in accordance with an embodiment.
Figure 6B:
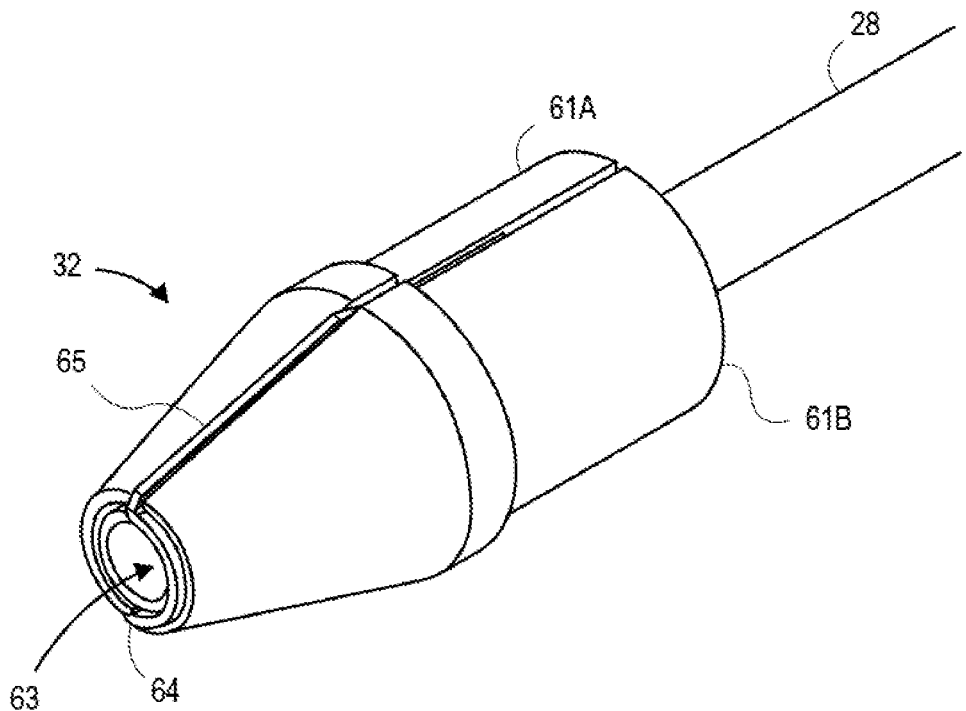
Figure 6D:
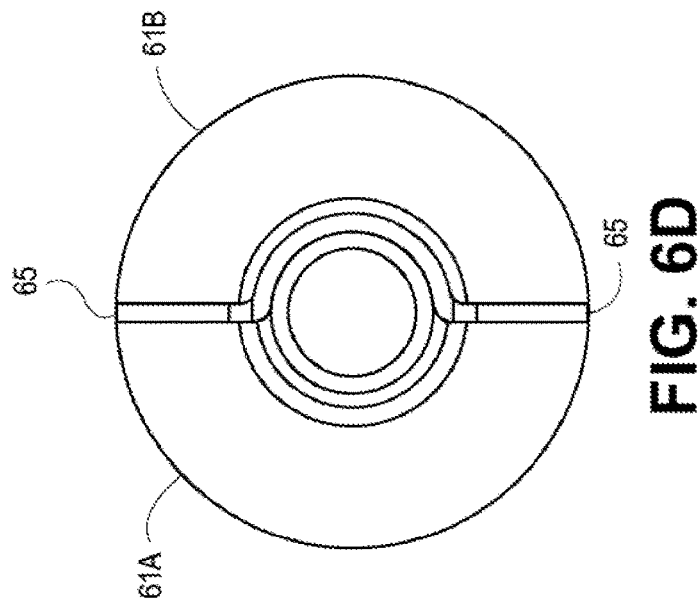
Figure 6C:
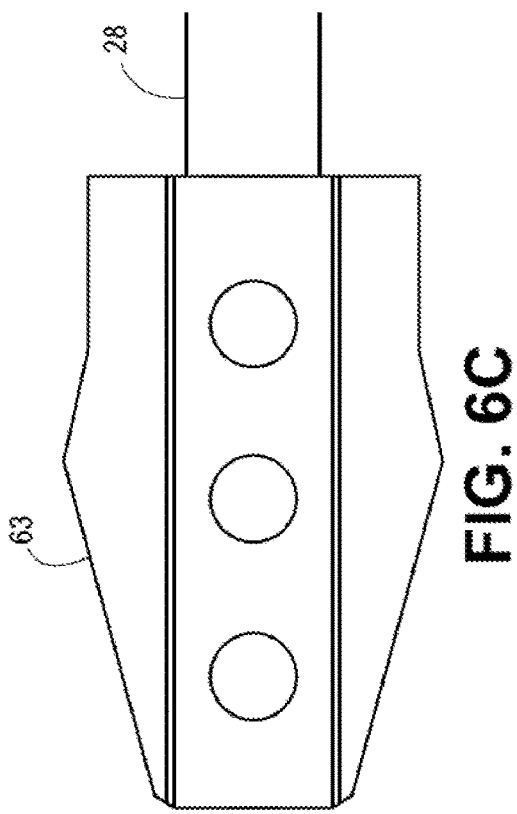
Figure 6E:
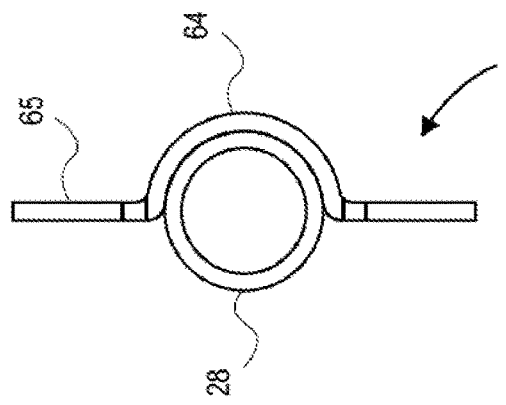
Figure 7B:
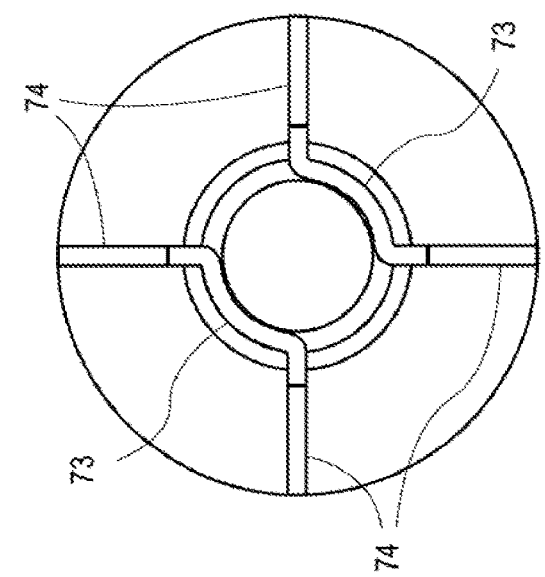
FIGS. 7A-7D illustrate various views of a distal tip in accordance with an embodiment.
Figure 7D:
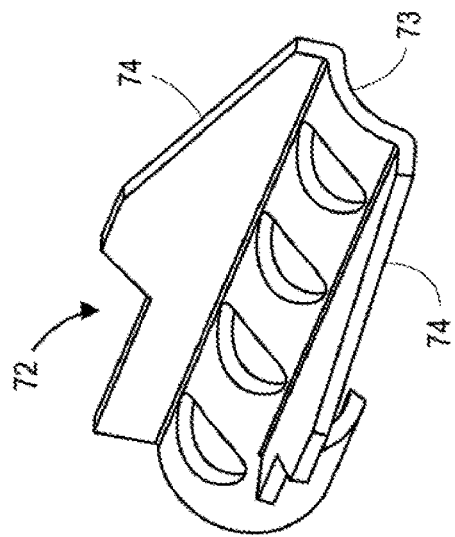
Figure 7A:
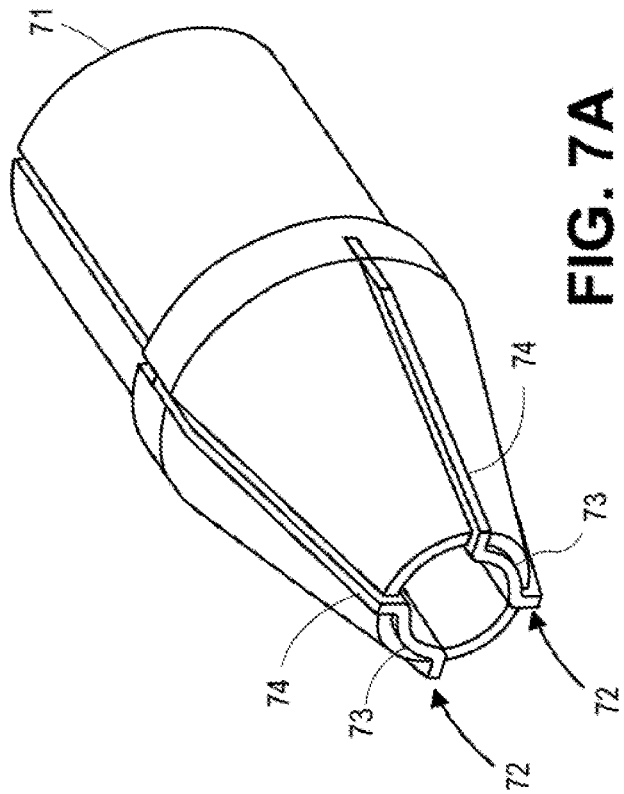
Figure 7C:
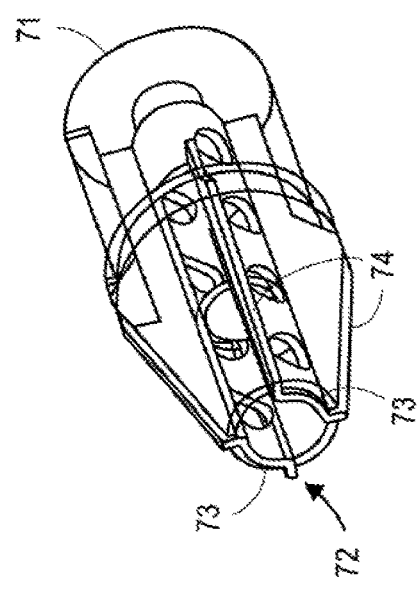

A proximal segment 44 of the tissue anchor stent 34 is now expanded by moving the second slide actuator 18 in the proximal direction to a position at or near the proximal end of the first slide actuator 15, after releasing lock 22 as in FIG. 5E to further retract the sheath 27. The proximal end of the tissue anchor stent 34 releases from stent lock 30 (FIG. 2A) as the second slide actuator 18 reaches the proximal end of its travel. This releases the entire tissue anchor, which in this example has a central lumen 46 allowing fluid communication between lumens L1 and L2. The device 10 is now removed, leaving the tissue anchor 34 with central lumen 46 implanted between lumen L1 and lumen L2 with fluid communication being established. The stent 34 can promote the formation of a healthy anastomosis between lumen L1 and lumen L2 by firmly holding tissues T1 and T2 together while minimizing damage to the tissue walls. The stent 34 can be removed at a later date.

The stent 34 is illustrated with a double walled flange structure. The configuration of the flanges and diameter and length of the central lumen 46 can be selected based on the body lumens L1 and L2 and the thickness of the tissue walls T1 and T2. A variety of stent shapes and materials can be used, such as the stent structures illustrated in FIGS. 18A-18E and described in greater detail below.

A variety of different tip designs can be used for the conductive portion and cutting elements. Additional tip designs are illustrated in FIGS. 3-15 and discussed in greater detail below.

In some embodiments, the devices disclosed herein have a smaller cutting surface area than prior art cone devices. The surface area of the external conductive portion illustrated in FIGS. 3A-3C is less than one sixth of the surface area for a cone having similar dimensions.

The blunt cone shaped tip was calculated to have a surface area of approximately 20.2 $mm^2$. The tip design in the embodiment illustrated in FIGS. 3A-3C was calculated to have a cutting surface area of about 3.17 $mm^2$. In some embodiments the conductive cutting portion of the distal tip has a surface area of less than about 10 $mm^2$. In some embodiments the conductive cutting portion of the distal tip has a surface area of less than about 5 $mm^2$. In some embodiments the conductive cutting portion of the distal tip has a surface area of less than about 4 $mm^2$.

The smaller cutting surface area will have a higher current density than a larger surface area (e.g. with a cone shape) for a given power. The higher current density on the cutting surface area can facilitate quicker cutting of the tissue. The faster cutting can minimize the thermal injury to the tissue that is cut along with adjacent tissue. Examples of thermal damage to tissue include coagulation, loss of elasticity of the tissue, denaturing of proteins, and necrosis. The devices disclosed herein can minimize tissue damage thereby maintaining tissue elasticity after cutting the tissue.

The devices disclosed herein can operate at a wide range of powers, for example from about 30 Watts to about 200 Watts or greater. In some embodiments about 50 Watts to about 100 Watts can be used to provide power to the conductive cutting surface. The reduced surface area of the cutting surface can facilitate the operation of the device at lower powers because the current running through the cutting surface area can still be high enough to cut through the tissue.

The devices disclosed herein can operate with a higher energy density, represented by the power divided by the surface area of the conductive cutting surface area, for a given power versus conventional cone shaped energized tip designs. The tip design in the embodiment illustrated in FIGS. 3A-3C was calculated to have an energy density of 9.4 Watts/$mm^2$ at a power of 30 Watts, 31.5 Watts/$mm^2$ at a power of 100 Watts, and 63.0 Watts/$mm^2$ at a power of 200 Watts. A conventional blunt conical shaped tip design was calculated to have an energy density of 1.5 Watts/$mm^2$ at a power of 30 Watts, 5.0 Watts/$mm^2$ at a power of 100 Watts, and 9.9 Watts/$mm^2$ at a power of 200 Watts. The calculated power density for the tip design illustrated in FIGS. 3A-3C was over six times higher than the power density for the same power supplied to a blunt conical shaped tip with similar dimensions.

In some embodiments the energy density of the conductive cutting surface area of the distal tip is between about 5 Watts/$mm^2$ and 100 Watts/$mm^2$. In some embodiments the energy density of the conductive cutting surface area of the distal tip is greater than about 10 Watts/$mm^2$. In some embodiments the energy density of the conductive cutting surface area of the distal tip is greater than about 30 Watts/$mm^2$. In some embodiments the energy density of the conductive cutting surface area of the distal tip is greater than about 60 Watts/$mm^2$.

The devices disclosed herein can also use a lower mass as less metal is used for the cutting surface and the other portions of the tip can be made out of lighter weight insulating materials such as ceramics, plastics, and other light-weight materials.

In some embodiments a scalpel-like cut through multiple tissue layers using HF current can be done. Some embodiments use a central HF powered feature located adjacent to the guidewire to form an initial cut into the tissue and HF powered projections extending out radially from the center feature to cut a slit in the tissue planes.

In some embodiments different frequencies or power can be supplied to different conductive areas on the tip. In some embodiments two or more conductive areas can be used, which can be supplied power by one or more power sources.

In some embodiments the devices disclosed herein can use a metallic ring (concentric or non-concentric in nature) or a segmented metallic ring (concentric or non-concentric in nature) with a projection or projections extending radially outward from the ring. The ring and projections are connected to the energy source, such as a RF or HF generator or energy source. The projections and central cutting feature may be connected to a single channel of an energy source. Alternatively, the projections and central cutting feature may be connected to two or more channels of an energy source or sources, such that different energy profiles may be applied to various features. A portion of the cutting features can be partially embedded in the insulating material.

In some embodiments the portion of the conductive area that is exposed at the outer surface of the distal tip can be segmented or discontinuous. In some embodiments the projections can be discontinuous or segmented. Each of the segments or discontinuous portions can be in electrical communication with each other and/or one or more electrical sources.

In some embodiments the central feature and projections do not include a ring. For example, the central feature and projections can be an arc extending from one side of the distal tip to the opposing side of the distal tip in an arc configuration.

In some embodiments the tip design includes one or more outward projections. In some embodiments one or more (1 . . . N) features or projections protrude in a radial fashion. The projections can have a linear design, curved or arced shapes, and other geometric shapes. Additional examples include a helical twist and interconnected rings from a central point or HF powered feature. Each feature would result in a linear cut in the tissue radiating outward from a central point. The (1 . . . N) features would result in (1 . . . N) cuts and subsequently N number of tissue leaflets or valve leaflets. In the case of a single feature, one linear feature creates 2 tissue leaflets. These leaflets in turn act as valves preventing excessive material transfer (fluid, tissue, matter) from passing from the target anatomical structure to the access structure or from the access structure to the target anatomical structure.

In some embodiments the devices can be used with a guidewire lumen or hole in the tip. The guidewire is shielded from the current supplied to the tip. The devices disclosed herein can follow a guidewire placed within the target anatomical structure. The guidewire can be placed in the target anatomical structure using a needle, such as a 19 gauge needle. The devices can follow the guidewire until the tip is at the target anatomical structure. Energy can be supplied to the tip of the device, such as radiofrequency (RF), high-frequency (HF), or other types of energy. An electrosurgical generator can be used to power the tip in some embodiments. The energized tip of the device can then cut through the tissue to create luminal access into the target anatomical structure. The high current density tip is designed to cut through a tissue plane resulting in minimal thermal injury to the tissue planes and timely access to the target anatomical structure.

In some embodiments the catheter devices and tip designs does not follow a guidewire with the energized tip used for initial access to the body lumens. In some embodiments the catheter devices do not include a guidewire lumen and can be used without a guidewire. In some embodiments the catheter devices can be positioned without a guidewire but may include a guidewire lumen for placing a guidewire after initial access to the body lumens.

The methods and devices disclosed herein can be used to cut in any angular catheter orientation. For example, the tip and cutting element can follow a guidewire and cut tissue orientated in any angle relative to the guidewire. The cutting element can cut tissue when the guidewire forms an acute angle with the tissue plane. Prior art blunt cone devices do not cut tissue well when they intersect the tissue at an acute angle and often cause tissue tearing and trauma while sliding along the tissue surface. The prior art blunt cones can also have a difficult time following a guidewire path at an acute angle with the tissue surface and undesirably change the shape and orientation of the resulting tissue penetration.

Minimal tenting and displacement of the tissue plane of the target anatomical structure is also desired. Minimizing the displacement and tenting of the tissue plane can help prevent excessive biological matter leakage and provide a level of safety given the path following the guidewire. In addition minimal displacement is important because if the tissue/target is moved significantly the physician may lose visibility of the field, in particular when visualization is done by ultrasound imaging.

A variety of distal tip 32 designs can be used in the devices disclosed herein. The tip designs disclosed herein can be designed to minimize or prevent leakage from the opening cut in the passage of the targeted anatomical structures given the large diameter of the catheter entering the anatomical structures. The tip can be designed to achieve a desired cut tissue pattern in the luminal walls. FIGS. 3A-3C illustrate a cutting element 35 with a concentric design and two projections 36 at about 180 degrees from each other. The cut pattern delivered by the tip illustrated in FIGS. 3A-3C can mimic a bi-leaflet valve opening while allowing the passage of the device through the tissue planes limiting biological material leakage across those tissue planes. FIGS. 17A-17H and 18 show examples of tissue cut patterns. In some embodiments the tissue cut pattern can be a bi, tri, quad . . . n leaflet valve opening type.

FIGS. 6A-6E illustrate various views of a distal tip 32 in accordance with an embodiment. The distal tip 32 is connected to the shaft 28. The distal tip 32 includes two insulating sections 61a and 61b with a cutting element 63 sandwiched between the sections 61a and 61b. The cutting element 63 includes a central cutting feature 64 with a semi-circular configuration and two outward projections 65. Electrical energy can be supplied to the cutting element 63 to cut tissue. The cutting element 63 can be stamped or machined in the desired configuration. The semi-circular configuration 64 can be sized to fit the outer diameter of the shaft 28. In some embodiments a second cutting element can be used with a shape mirroring the cutting element 63 to form a circular cutting feature. In some embodiments wire can be used to form a circular conductive feature about the shaft 28 at the distal portion of the cutting element 63. The design illustrated in FIGS. 6A-6E can be manufactured from a stamped metal such as stainless steel and co-molded with an insulating material to form the remainder of the distal tip 32.

FIGS. 7A-7D illustrate various views of a distal tip 32. The distal tip 32 includes an insulating portion 71 and two cutting elements 72 in accordance with an embodiment. Each cutting element 72 includes a central cutting feature 73 with an arced configuration and outward projections 74.

Electrical energy can be supplied to the cutting element 72 to cut tissue by connecting a wire to the cutting element. The cutting element 72 can be stamped or machined to form the desired configuration. The arced configuration 73 can be sized to engage with the outer diameter of the shaft. In some embodiments more than two cutting elements 72 can be embedded in the tip. In some embodiments three or four cutting elements can be embedded in the distal tip.

FIGS. 8A and 8B illustrate various views of a distal tip 32 in accordance with an embodiment. The distal tip 32 includes an insulating portion 81 and a cutting element 82. The cutting element 82 includes a central cutting feature 83 with a circular shape and outward projections 84. The outward projections extend outwardly towards the outer diameter of the tip 32 in a helical configuration. The projections 84 extend radially to an outer diameter that is less than the outer diameter of the insulating portion 81. FIGS. 8A and 8B illustrate a clockwise spiral for the projections 84. A counter clockwise spiral configuration can also be used. In some embodiments the projections can be straight. In some embodiments the projections can have a sinusoidal configuration. Electrical energy can be supplied to the cutting element 82 to cut tissue by connecting a wire to the cutting element.

Figure 9A:
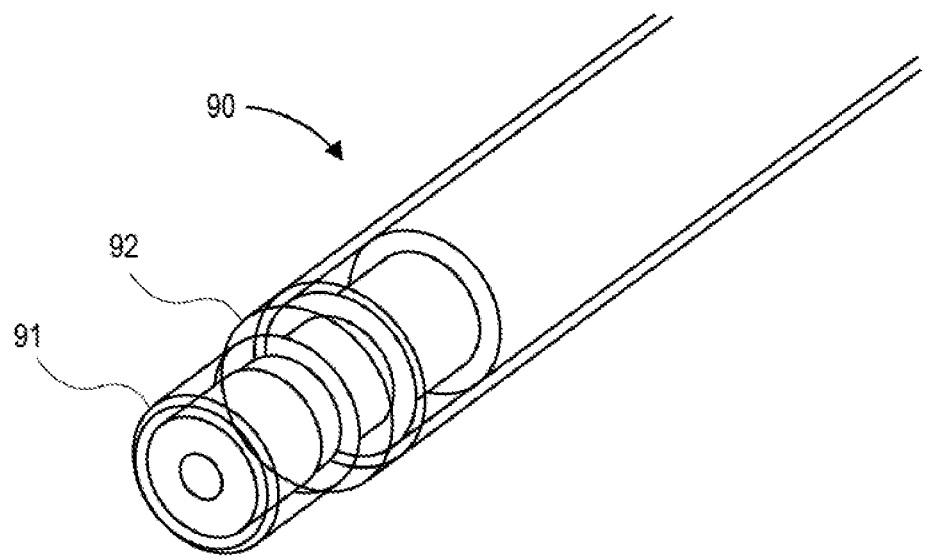
FIGS. 9A-9B illustrate various views of a distal tip in accordance with an embodiment.
Figure 9B:
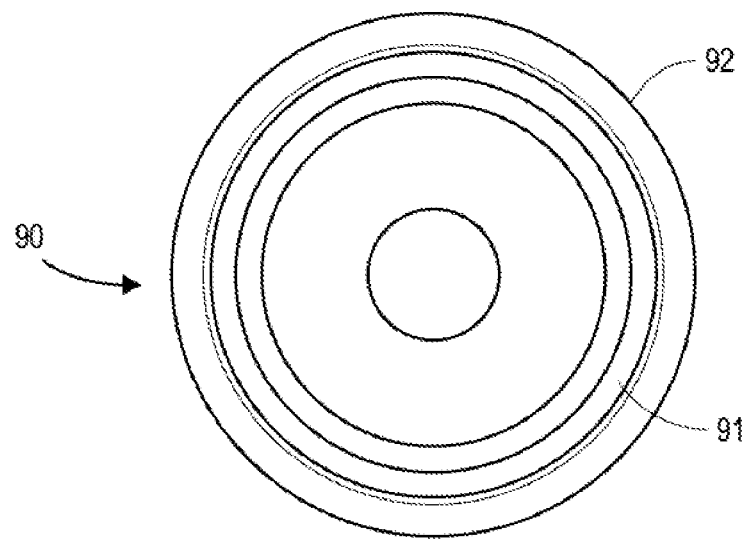

FIGS. 9A and 9B illustrate a distal end of a catheter device 90 with multiple rings 91, 92 in accordance with an embodiment. The inner ring 91 and outer ring 92 can be energized by electrical energy. The inner ring 91 and outer ring 92 can have separate wiring and electrical power sources. The power and type of electrical energy provided to the inner ring 91 and outer ring 92 can be different and separately controlled for each ring. The inner ring 91 can be used to make the initial access hole in the body lumen or enlarge an initial penetration formed by a needle. The outer ring 92 can be used to enlarge the passageway formed by the inner ring 91.

Figure 10A:
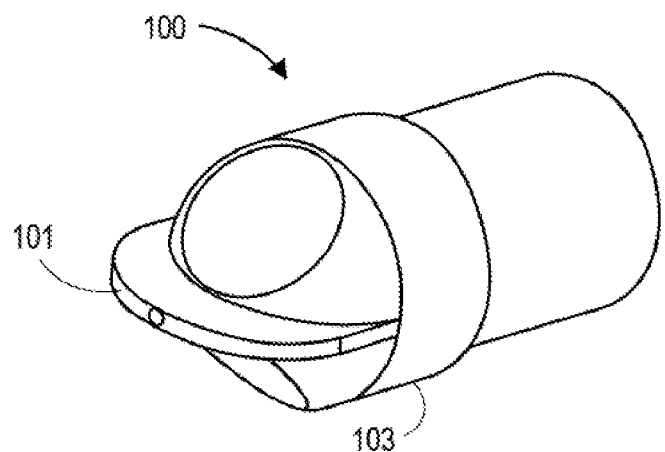
FIGS. 10A-10B illustrate various views of a distal tip in accordance with an embodiment.
Figure 10B:
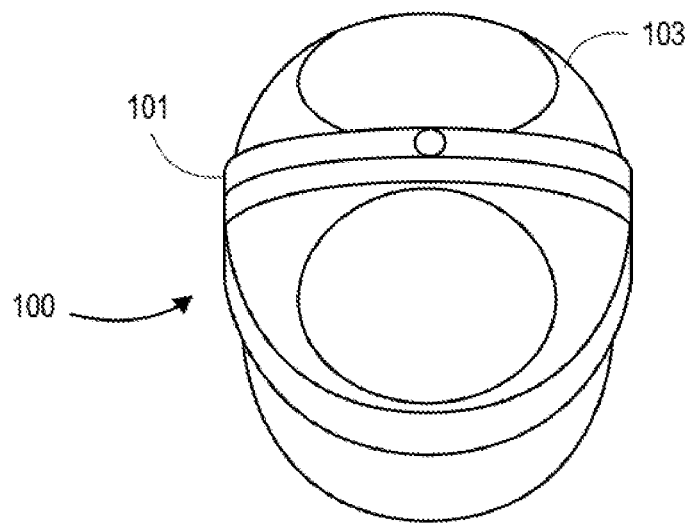
Figure 11A:
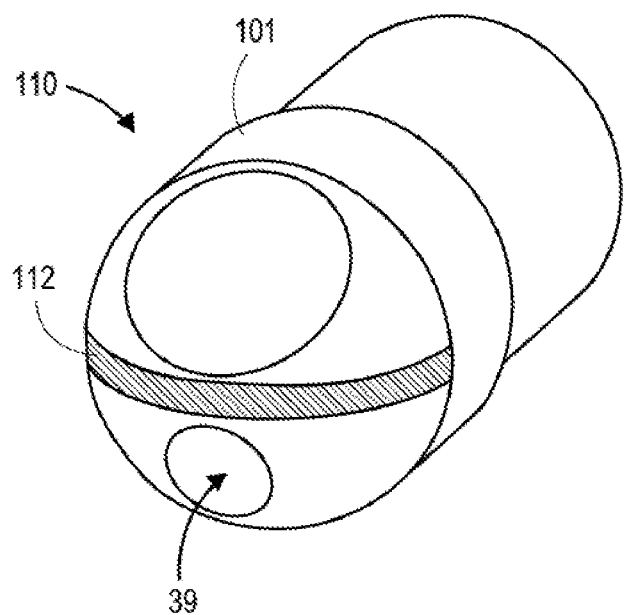
FIGS. 11A-11B illustrate various views of a distal tip in accordance with an embodiment.
Figure 11B:
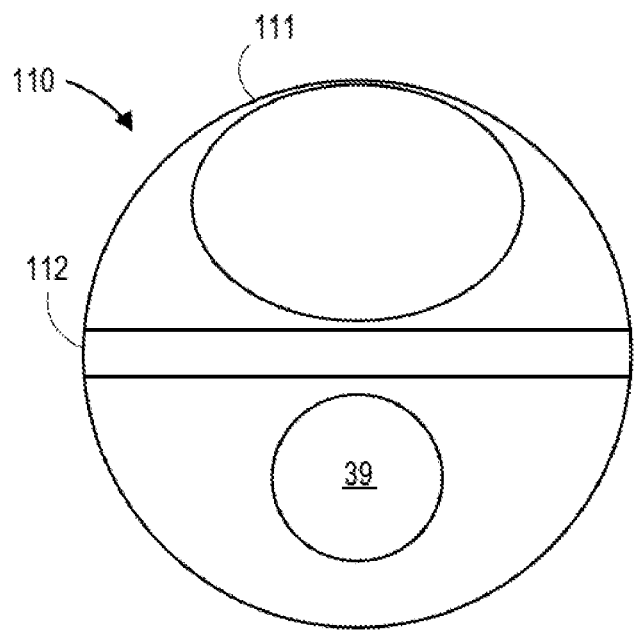

FIGS. 10A and 10B illustrate a distal tip of a catheter device 100 in accordance with an embodiment. The distal tip has a cutting feature 101 made out of a conductive material and an insulating portion 103. The device 100 is configured to be used without a guidewire. Electrical energy is supplied to the cutting feature 101 to cut tissue. FIGS. 11A and 11B illustrate a distal tip of a catheter device 110 similar to catheter device 100 but with a guidewire lumen 39 offset from the center of the catheter device 110 in accordance with an embodiment. The catheter device 110 includes an insulating portion 111 and cutting feature 112.

Figure 12A:
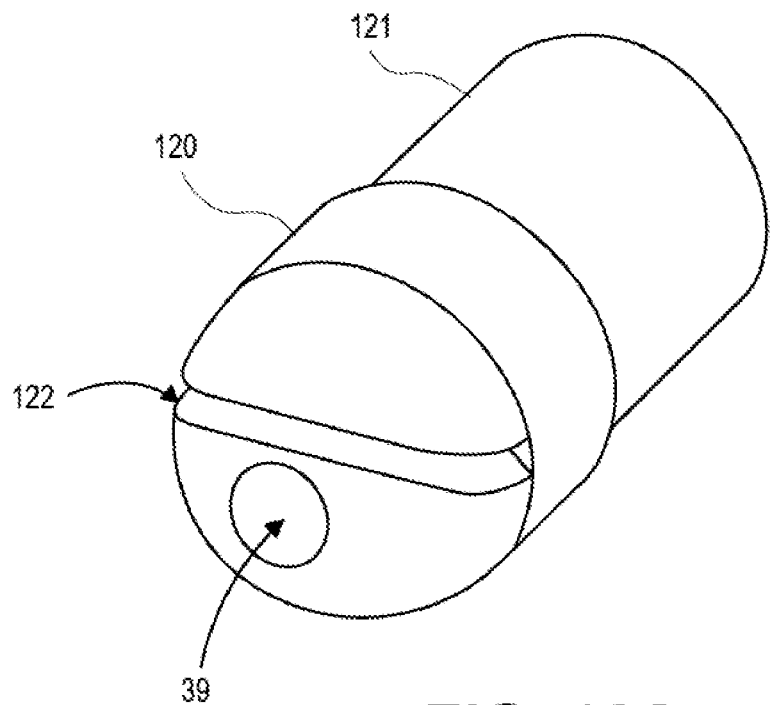
FIGS. 12A-12B illustrate various views of a distal tip in accordance with an embodiment.
Figure 12B:
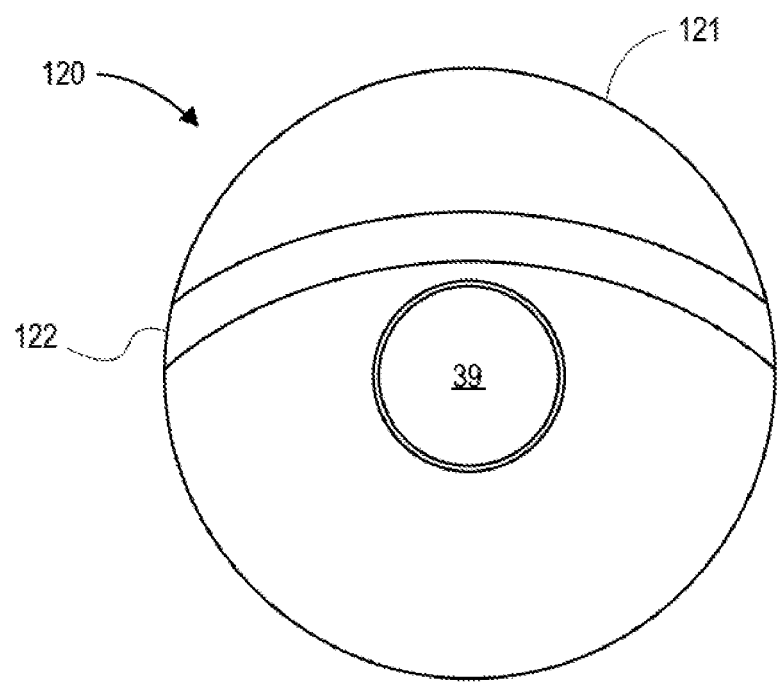

FIGS. 12A and 12B illustrate a distal tip of a catheter device 120 in accordance with an embodiment. The distal tip has a cutting feature 122 made out of a conductive material and an insulating portion 121. The catheter device includes a guidewire lumen 39. The cutting feature 122 is offset from the center of the distal tip and has an arced configuration.

Figure 13C:
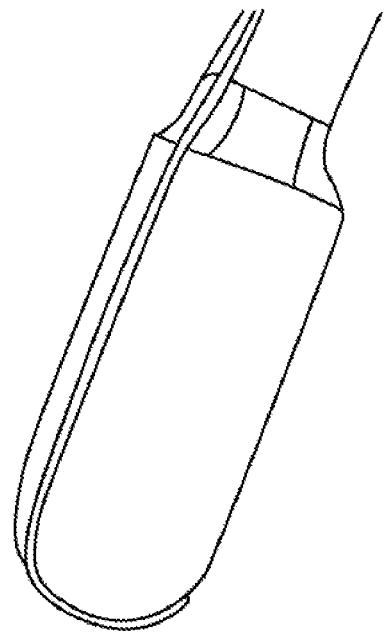
FIGS. 13A-13C illustrate additional distal tip designs in accordance with embodiments.
Figure 13A:
Figure 13B:
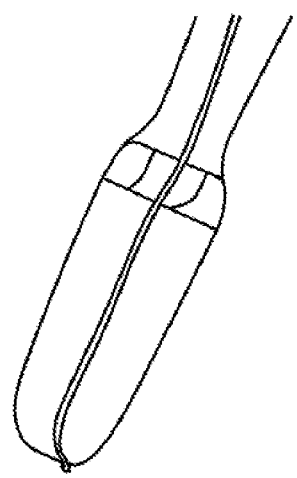

In some embodiments the catheter devices do not have a guidewire lumen. The catheter device can locate the target tissue without following a guidewire. The energized tip can then be used for the initial penetration in the target tissue. FIGS. 13A-13C illustrate portions of the tips of catheter devices that can be utilized without a guidewire. FIG. 13A illustrates a distal tip with a dome shaped tip with a metal cutting element extending from the dome. FIG. 13B illustrates a cone shaped distal tip with a conductive wire cutting element bent over the distal tip. FIG. 13C illustrates a dome shaped distal tip with a conductive wire cutting element bent over the dome shaped distal tip.

Figure 14A:
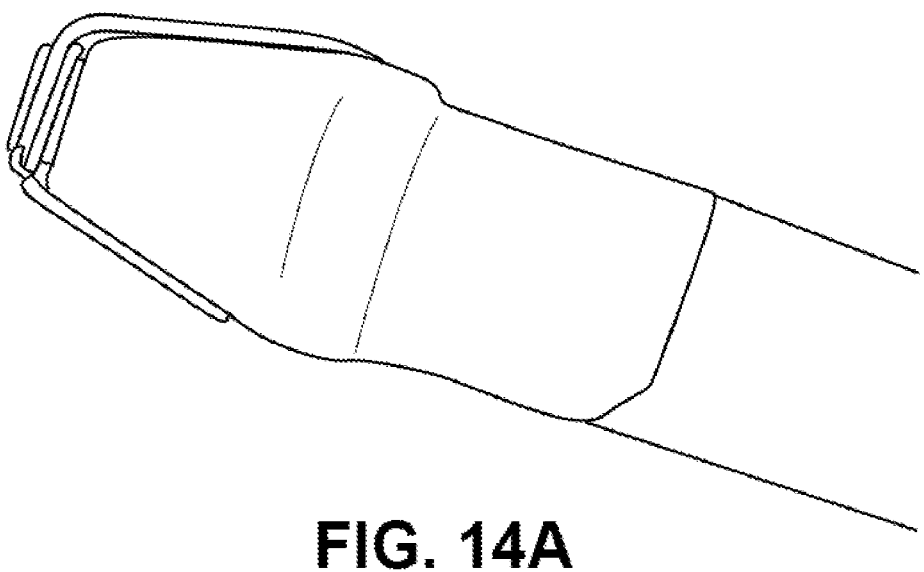
FIGS. 14A-14D illustrate additional distal tip designs in accordance with embodiments.
Figure 14B:
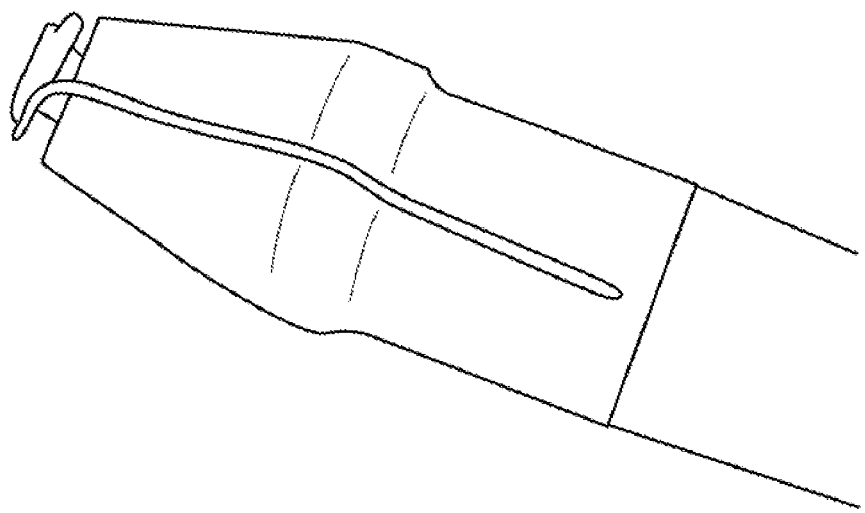
Figure 14C:
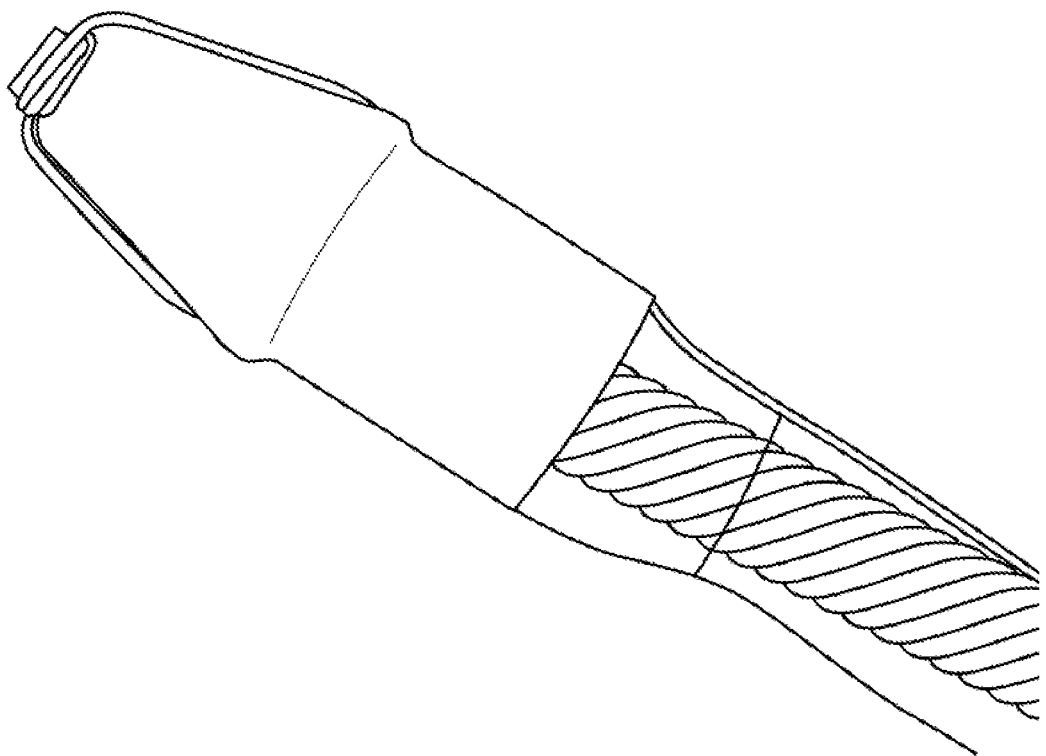
Figure 14D:
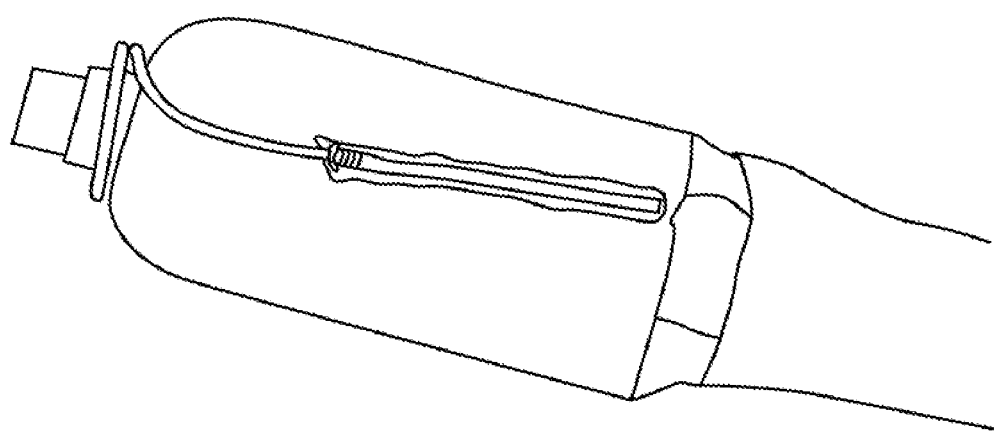

FIGS. 14A-D are images of ring shaped cutting elements with outward projections. FIGS. 14A-14B illustrate a cutting element formed using stainless steel wire having a diameter of 0.006" and a ceramic cone shaped tip. The outward projections are recessed into the ceramic cone near the outer diameter of the cone. In tests the cutting elements efficiently cut through tissue with little to no damage or coagulation outside of the cut area. FIG. 14C illustrates a tip design similar to the FIGS. 14A-B with stainless steel wire wrapped around a distal portion of a guidewire lumen shaft. Stainless steel wire is used for the exterior portions of the wire and copper wiring is used for the internal wiring. FIG. 14D illustrates a distal tip with a copper wire wrapped over a circular stainless steel electrode disposed about a guidewire lumen shaft. Examples of nose cone shapes include cone shapes and bullet shapes.

Figure 15B:
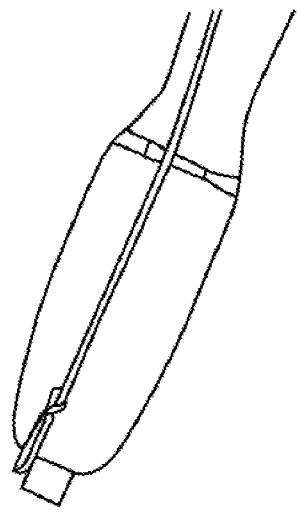
FIGS. 15A-15F illustrate additional distal tip designs in accordance with embodiments.
Figure 15A:
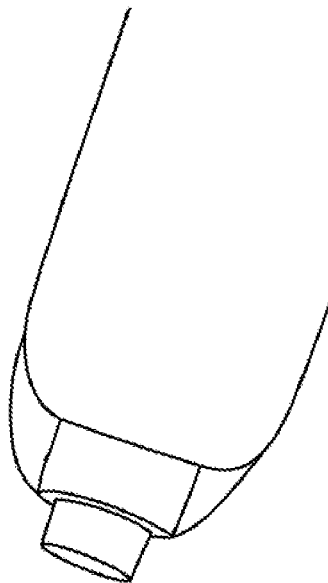
Figure 15D:
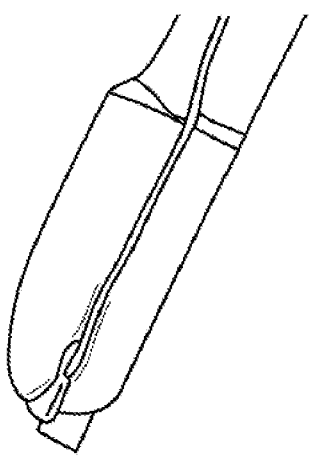
Figure 15C:
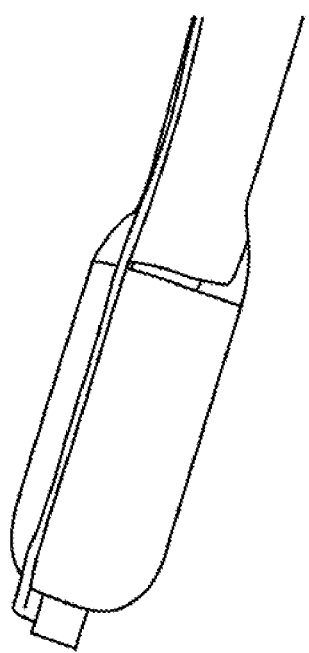
Figure 15F:
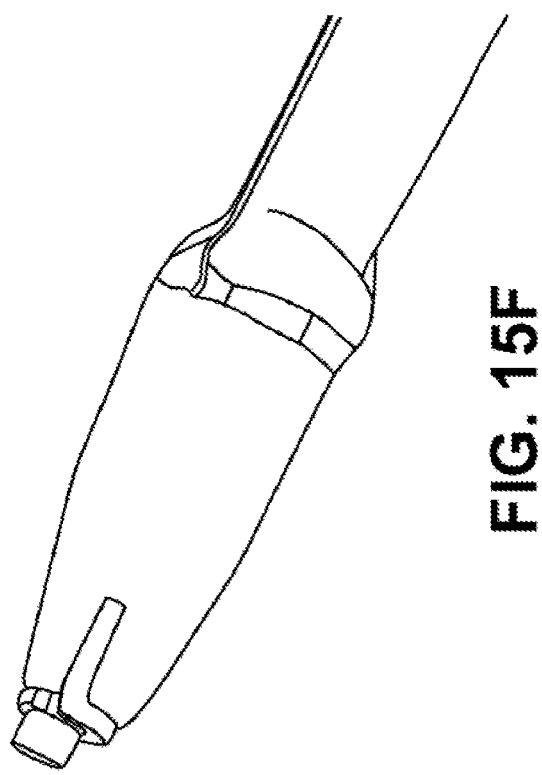
Figure 15E:
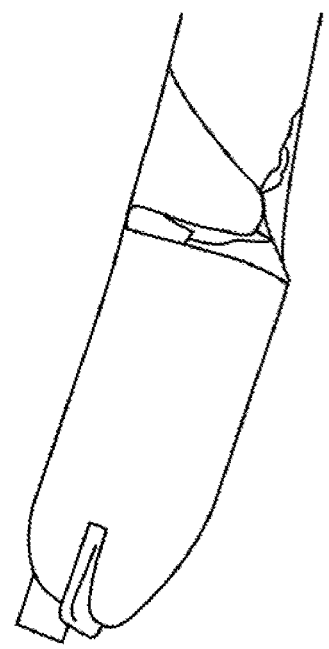

FIGS. 15A-F are images of additional distal tip designs. FIGS. 15A-15F illustrate guidewire lumen shafts and cutting elements having different configurations. FIG. 15A is an image of a dome shaped tip with a cutting element connected to a copper wire with the cutting element offset from the guidewire lumen shaft. FIG. 15B is an image of a dome shaped tip with a cutting element disposed about the guidewire lumen shaft with wings extending towards the outer diameter of the bullet shaped ceramic tip. FIG. 15C is an image of a cone shaped tip with a cutting element connected to a copper wire with the guidewire lumen shaft offset from the central portion of the distal tip. FIG. 15D is an image of a cone shaped tip with a cutting element connected to a copper wire with the cutting element offset from the guidewire lumen shaft. FIG. 15E is an image of a dome shaped tip with a stainless steel cutting element adjacent to the guidewire lumen shaft. FIG. 15F is an image of a nose shaped tip with a cutting element concentric to the guidewire lumen shaft.

Figure 16C:
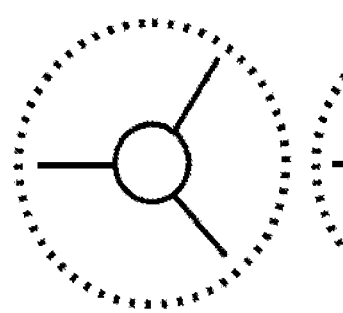
Figure 16D:
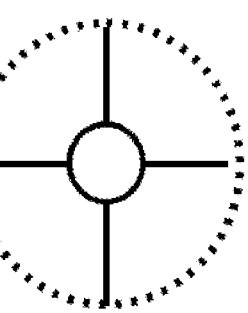
Figure 16E:
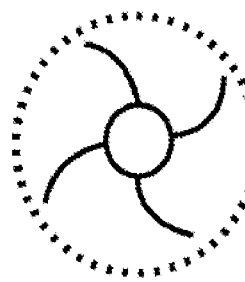
Figure 16F:
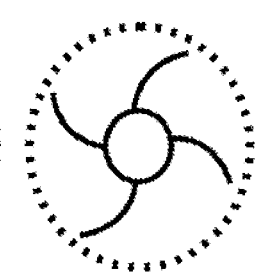
Figure 16G:
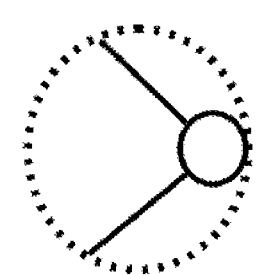
Figure 16H:
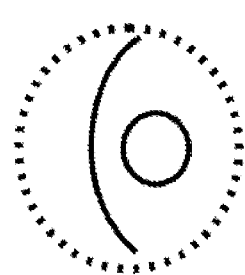

FIGS. 16A-16H illustrates various tissue access patterns made by the different energized tip configurations disclosed herein. The dotted lines in FIGS. 16A-16H correspond to the outer diameter of the catheter shaft. FIG. 16A illustrates a tissue cutting or access pattern generated by an offset ring and one outer projection. FIG. 16B illustrates a tissue cutting pattern generated by a central cutting feature with two outward projections. FIG. 16C illustrates a tissue cutting pattern generated by a central cutting feature with three outward projections. FIG. 16D illustrates a tissue cutting pattern generated by a central cutting feature with four outward projections. FIGS. 16E and 16F illustrate tissue cutting pattern generated by a central cutting feature helical projections extending counter clockwise and clockwise, respectively. FIG. 16G illustrates a tissue cutting pattern generated by an offset cutting feature with two outward projections. FIG. 16H illustrates a tissue cutting pattern generated by an offset cutting feature with an offset arc element. FIG. 17 is an image of a tissue access pattern generated using the distal tip and cutting features illustrated in FIGS. 3A-3C.

In some embodiments, as shown, the distal tip 32 can be conically shaped and can have the same outer diameter as the outer diameter of catheter body 12. In other embodiments, the distal tip can be a truncated cone, a cylinder, a rounded cylinder, semi-spherical, triangular, beveled, wedge shaped, or any other suitable shape for penetrating tissue. In some embodiments, a ceramic insulating ring can be placed between the distal tip and the catheter body and/or between the tip and the stent or any onboard needle to prevent the tip from heating and/or melting the catheter, stent, and any onboard needle. In some embodiments, the distal tip can be tapered as finely as possible (e.g., cone or bougie-shaped) so as to minimize step-off between the guidewire and the distal tip. Any of the distal tip and cutting element designs disclosed herein can be used.

In some embodiments the devices disclosed herein can be used with a guidewire having an anchor structure as disclosed in co-owned application U.S. Patent Publication No. 2010-0268029, which is incorporated by reference herein in its entirety. The anchor structure can be a shape memory alloy, for example, so that it can be configured to automatically expand to a predetermined shape upon being advanced distally from a needle.

In some embodiments, the catheter is disposed within an endoscope, and in other embodiments, the catheter is an endoscope or takes the place of an endoscope.

The devices and methods disclosed herein can be used in a variety of applications and for obtaining access between a variety of different body lumens. In some embodiments the devices disclosed herein can be used for cross-luminal drainage.

In some embodiments an anastomosis or fistula can be formed using the devices and methods disclosed herein. For example, a stent can be placed between two body lumens to provide fluid communication between the two body lumens. The two adjacent body lumens can form an anastomosis as they heal around the stent.

The devices and methods can be used in the gastrointestinal (GI) tract and areas adjacent to a portion of the GI tract. Examples of anatomy in the GI tract include the esophagus, stomach, duodenum, jejunum, small intestine, and large intestine. Non-limiting examples of portions adjacent to the GI tract include the peritoneal cavity, bile duct, pancreatic duct, gall bladder, pancreas, cysts, pseudocysts, abscesses and the like.

In some embodiments the devices and methods can be used in the urinary tract (e.g. urinary bladder and ureter), pulmonary tract (e.g. trachea and bronchi), biliary tract (e.g. bile duct and gallbladder), and for vascular applications.

The body lumens can be any organ that can be accessed endoscopically and can be a hollow or solid organ, duct, vessel, or soft tissue structure. Examples of first and second body lumens include the esophagus, stomach, duodenum, jejunum, small intestines, large intestines, colon, bile duct, pancreatic duct, gallbladder, crus muscle, fundus, cysts, pseudocysts, abscesses, pancreas, liver, urinary bladder, rectum, sinus cavity, heart, lung, etc.

The methods and devices disclosed herein can be useful for a variety of medical procedures. Embodiments can be applied to ERCP applications where there is a need to access target anatomical structures through multiple tissue planes from a guidewire access. Embodiments are useful for applications and procedures, such as gastrojejunostomy, gastroduodenostomy, gastrocolostomy, transduodenal, transgastric, biliary, pancreatic pseudocysts, transhepatic, transcystic, transpancreatic, transenteric, transbiliary, gastroplexy, cystoplexy, transsesophageal, transbronchial, transgastric, colon resection, gastric bypass, jejunostomy, etc.

The methods and devices disclosed herein can also be used for cross-luminal therapy or access to body lumens to provide further treatment, such as chemotherapy, placing sensors, placing treatment delivery devices, providing pharmaceutical devices, radioisotope treatment, and others. The access to the body lumens can be through the stent or other device placed in or adjacent to the body lumen of interest for the targeted treatment. The stent can also include additional therapeutic agents, such as pharmaceutical agents, radioactive agents, and other therapeutic agents. The therapeutic agents can be impregnated in the stent or included as a coating. In one example, a stent can be placed next to or adjacent to a tumor. The tumor can be treated with targeted chemotherapy. The chemotherapy can be introduced using the stent or using the stent passageway to facilitate treatment.

In some embodiments the methods and devices can be used for peritoneal access and TIPS (transjugular intrahepatic protosystemic shunt). In some embodiments the methods and devices can be used in applications and procedures, such as for vascular access, arterial to vascular, pericardial access, and venus insufficiently via transvalve access.

One application of particular interest in advanced therapeutic endoscopy is the drainage of bile from the gallbladder into the duodenum or stomach. This is accomplished endoscopically from within the GI lumen of the duodenum or stomach and requires that the gallbladder be located using transluminal imaging, such as endoscopic ultrasound (EUS), followed by penetration through the GI lumen and gallbladder wall and precise placement of a drainage stent between these structures. During the placement of the drainage stent, it is necessary that close apposition of the gallbladder and GI lumen be maintained to prevent bile leakage into the peritoneal cavity, a situation that can cause peritonitis which can be fatal. In this instance, delivery of a tissue anchor or luminal approximating stent requires precise control allowing that close apposition is maintained throughout the procedure and throughout the course of therapy. Using the devices disclosed herein, tissue stents and anchors can be precisely delivered.

The devices disclosed herein can be used for bariatric surgery for gastric bypass and colon resection surgeries. For example, a stent can be delivered between the fundal pouch formed in gastric bypass surgery and a section of the duodenum or jejunum to form an anastomosis. For colon resection surgery a stent can be placed between two sections of the colon to form an anastomosis. The stent and resulting anastomosis can limit leakage, limit the formation of strictures, and create a standard size stoma or anastomosis. For bariatric surgery and colon resection surgery a blocked anastomosis or decreased anastomosis sizes can result in complications with fluid flow and solid food flow. Forming a standard size anastomosis can promote fluid and communication and decrease complications from blocked or too small anastomoses. The anastomosis size would correspond to the stent size so the variability in the anastomosis size would be greatly decreased over current surgical practices that involve manually stapling the tissue together to form the anastomosis.

The devices disclosed herein can be used to treat metabolic conditions, such as diabetes. Food is first churned in the stomach before passing into the small intestine. When the lumen of the small intestine comes into contact with nutrients, a number of hormones are released that can inhibit further food intake and have thus been dubbed "satiety factors". Changes in circulating hormone levels after gastric bypass have been hypothesized to produce reductions in food intake and body weight in obese patients. The devices can be used to make physical changes in the patient that can change hormonal balances that can improve the health of a patient, such as the "satiety factors". For example, diabetes can be treated through procedures such as a Roux En Y gastric bypass or gastrojejunostomy as described herein. The devices disclosed herein can be used in laparoscopic assisted procedures. The devices disclosed herein can be used with ear, nose, and throat (ENT) delivery. The devices disclosed herein can be used in Natural Orifice Transgastric Endoluminal Surgery (NOTES). The devices disclosed herein can be used with procedures that clamp or rivet tissue.

In some embodiments the devices disclosed herein can be used to close an opening in mammalian tissue. For example, a tissue anchor or stent with a closed lumen could be placed to seal an opening.

The devices disclosed herein can be used for access without delivering and placing a stent. For example, the devices can be used for a necosectomy to remove necrosed tissue as in the case of a necrotizing pancreatitis.

The devices disclosed herein can also be used to perform a cystotome. The device can be positioned adjacent to the target tissue, e.g. the transgastric or transduodenal wall. Electrical energy can be supplied to the conductive surfaces of the distal tip of the device to electrosurgically puncture a hole in the transgastric or transduodenal wall along with puncturing a pancreatic pseudocyst. The pancreatic pseudocyst can be visibly bulging into the GI tract. The distal tip can be supported by an inner catheter shaft within an outer tubular body of the catheter. The distal tip and inner catheter shaft can move relative to the outer tubular body of the catheter. After puncturing the target areas, e.g. transgastric or transduodenal wall and a pancreatic pseudocyst, the distal tip and inner catheter can be removed thereby leaving the outer tubular body of the catheter within the passageway formed when puncturing the transgastric or transduodenal wall and a pancreatic pseudocyst. The outer tubular body can be used as a working channel for access for additional medical tools. For a cystotome, a drainage kit or stent can be delivered through the outer tubular body to the pseudocyst. The devices disclosed herein have advantages over using a needle for initial access to the pseudocyst location because needle sizes can be limited to smaller thicknesses in order for the needle to maintain the desired flexibility and properties. In contrast, the catheter devices disclosed herein can be used to form an initial passage with a larger working channel than conventional needle procedures. In some embodiments, the outer tubular body can have a diameter of greater than 10 French. For example, the outer tubular body can have an 11 French diameter to leave a large working channel in body lumen. Positioning the catheter for the cystotome can be done without a guidewire. In some cases a guidewire can be used for positioning.

Various stent shapes and designs can be delivered using the devices and methods disclosed herein. FIGS. 18A-F, 19A-19I, 20A-20B, 21A-21D, and 22A-22B illustrate various stent designs that can be used with the devices disclosed herein. Additional stent designs are disclosed in co-owned U.S. Patent Publication 2009-0281557, previously incorporated by reference herein. The tissue anchors and stents include a body formed from a woven filament braid. The filament will typically be a metal wire, more typically being a nickel-titanium or other super-elastic or shape memory metal wire. The body can have both an elongated tubular configuration (FIG. 2A) and a foreshortened configuration where proximal and distal ends of the body expand radially into flange structures, as illustrated in FIG. 5E. The stents can expand radially to form a pair of adjacent annular rings which define the flange structures. After such foreshortening and deployment of the flange structures, the body will further have a cylindrical saddle region between the flange structures. When the anchor is deployed in tissue, the flange structures engage the outer surfaces of adjacent tissue layers (e.g. tissue T1 and tissue T2 illustrated in FIGS. 5A-5E) and the saddle region typically resides within a penetration through the tissue layers. The flange structures can have various configurations, including one or more inflection points to provide additional structural support to the stent flanges.

FIGS. 18A-F illustrate various configurations of the flanges 191 in double-walled configurations. In FIG. 18A, the flanges 191 expand radially. The central saddle region 192 has a length L and a diameter d. The flanges 191 have a diameter D. The stent 34 has lips or cuffs 193 on either end. The cuffs 193 have a diameter d'. FIG. 18A illustrates a covering or membrane 194 over the entire exterior of the stent 34. The cover or membrane inhibits tissue ingrowth and minimizes fluid leakage when the stent is implanted. The cuffs 193 have a diameter d' that is slightly larger than the diameter d of the central saddle region 192 in FIG. 18A. In FIG. 18B, the stent 34 has a cuff 193 diameter d' that is approximately the same as the diameter d of the central saddle region 192. In FIG. 18C, the stent 34 has a smaller diameter d than the stents illustrated in FIGS. 18A and 18B. FIG. 18C illustrates a cuff 193 diameter d' that is approximately the same as the diameter d of the central saddle region 192.

In FIG. 18D, a stent 34 having a central saddle region 192 with an expanded diameter d and smaller cuff 193 diameter d' is illustrated. In FIG. 18E, a stent 34 having a central saddle region 192 with an expanded diameter d and cuff 193 is illustrated. FIG. 18E has a greater cuff 193 diameter d' than the stent 34 illustrated in FIG. 18D. FIG. 18F illustrates a stent 34 without a cuff.

FIGS. 19A-19I illustrate cross sections of a quarter portions of stents with flanges 191 and central saddle regions 192. Each of the quarter portions are paired with a similar shape to form the entire flange 191. Each of the flange structures 191 can be paired with any of the other flange structures disclosed herein to form a stent with two flanges. FIG. 19A illustrates a flange with multiple inflections. FIG. 19B illustrates a flange 191 with multiple inflection including multiple flanges. FIG. 19C illustrates a flange 191 with the stent curved back towards the central saddle region. FIG. 19D illustrates a flange 191 with the stent curved away from the central saddle region 192. FIG. 19E illustrates a flange 191 with multiple inflections. FIG. 19F illustrates a flange 191 with a circular configuration. FIG. 19G illustrates a flange that curves towards the opposing flange and back on itself. FIG. 19H illustrates a flange 191 with notches or ribs in portions of the stent cross-section. FIG. 19I illustrates a flange 191 with a sinusoidal section to provide additional strength.

Figure 20B:
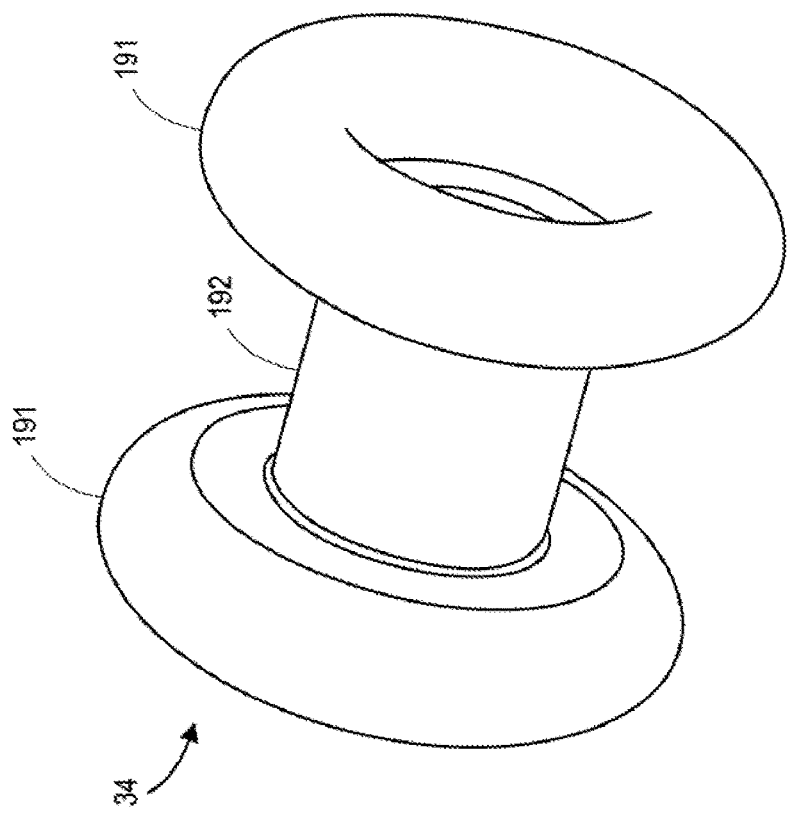
FIGS. 20A-20B illustrate a stent configuration in accordance with an embodiment.
Figure 20A:
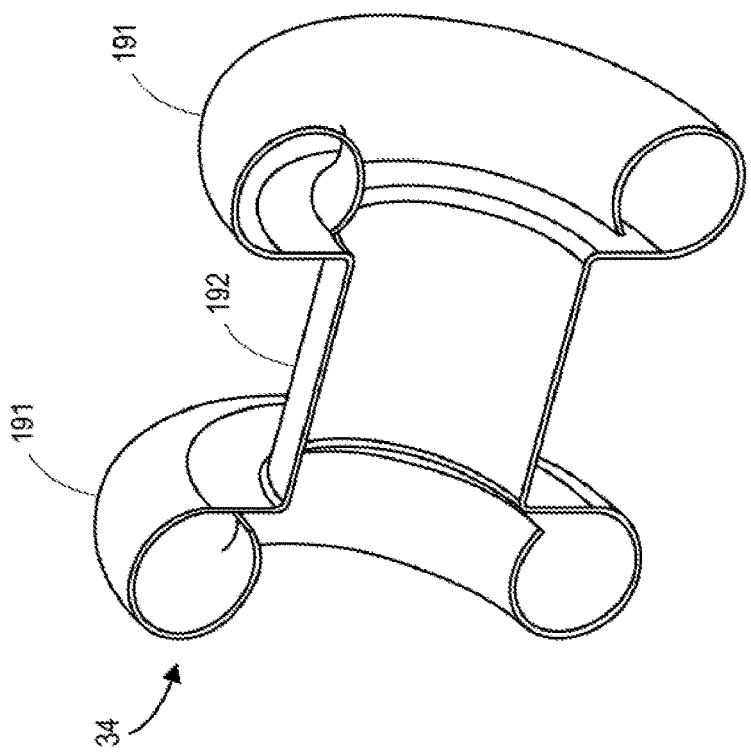
Figure 21B:
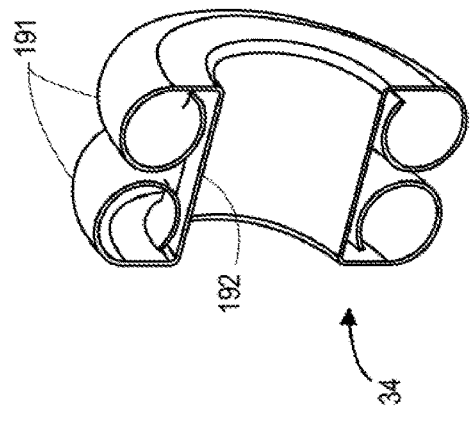
FIGS. 21A-21D illustrate various configurations of stents that can be delivered using the devices disclosed herein in accordance with embodiments.
Figure 21D:
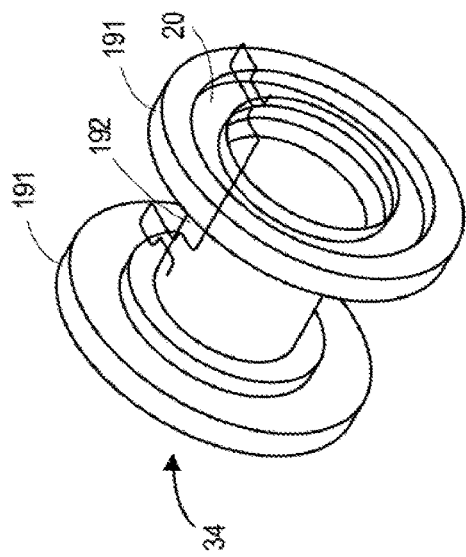
Figure 21A:
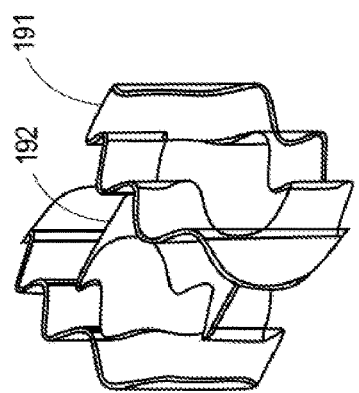
Figure 21C:
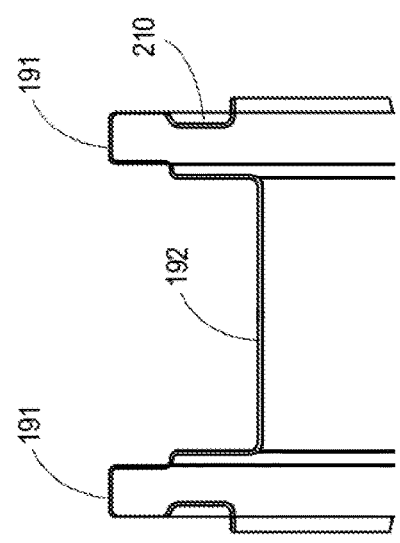

FIG. 20A is a cross-section of the stent illustrated in 20B. The flanges 191 have are inflected with a circular configuration that curves back towards the central saddle region. FIG. 21A illustrates a stent with flanges 191 that have sinusoidal configuration across the cross section of the flange. FIG. 21B illustrates a stent with flanges 191 that curve towards the opposing flanges and the central saddle region 192. FIG. 21C is a cross section of the stent illustrated in FIG. 21D. The stent has a flange 191 with a notch/rib 210 incorporated into the cross section of the rib.

The diameter D of the flanges 191 and the diameter d of the central saddle region 192 can be selected to allow the desired strength and fluid communication between the body lumens. For example, the diameter d should be large enough to allow for fluid communication between the body lumens. In some cases liquid flows through the central saddle region 192. In other cases particulate matter or solids can flow through the central saddle region 192. The diameter d should be sized to allow for the expected fluids and/or solids to flow through the saddle region 192. The diameter d can also be sized with a diameter close to the size of the hole in the body lumens to reduce the chance of leakage and improve stent engagement with the holes in the body lumens. The cuff length, diameter (d'), and shapes can be configured to achieve the desired physical properties in the stent. For example, the cuff can provide additional strength to the stent structure. The cuff can also have an increased diameter to make it easier for subsequent access to the interior volume of the stent with additional medical instruments or with a device to remove the stent. The tissue anchors of the prior art, such as metal clamps and rivets, have often been either too rigid, providing good attachment but presenting substantial risk of tissue necrosis or adhesion, or too weak, presenting little risk of tissue damage but allowing leakage and movement at the point of tissue penetration. The stents and tissue anchors disclosed herein can provide firm attachment of tissue while minimizing the risk of necrosis and other damage to the tissue. The stents disclosed herein provide enough pressure to hold the tissue walls together with the expanded flange structures but not too much force that can cause trauma to the tissue walls.

The stents disclosed herein can be used to form an anastomosis between the body lumens. Reducing the damage to the tissue during implantation of the stent and minimizing necrosis of tissue can promote tissue healing and expedite the formation of a healthy anastomosis.

Prior art stent designs for implantation in vascular applications are designed to be delivered to the target location and held in place permanently. The vascular stents are not designed to be removed or moved after implantation. In contrast to prior art vascular stents, the stents disclosed herein can be removed. The tissue anchors disclosed herein are also removable, both during initial implantation procedures as well as in a subsequent procedure(s) many weeks, months, or even years following the initial implantation.

The stents can include a coating to prevent tissue in-growth. Preventing tissue in-growth in the stent makes removal of the stent easier. Coatings can also be used to provide a smooth outer surface of the stent and to reduce friction against the tissue when deploying and removing the stent. The coating can reduce or eliminate voids in the stent structure and prevent tissue in-growth. The collapsibility of the stent also facilitates removal. The double walled flange structure can also make removal of the stent easier because the flange structures are easier to grab using medical tools. In some embodiments a snare can be used to grab one of the double walled flanges of the stent. Pulling on the flange can collapse the stent structure to compress the stent and allow for easy removability of the stent after formation of the anastomosis.

The length of the saddle region can be optimized based on the thickness of each of the tissue walls such that the flanges securely engage and hold the tissue planes together. Each of the flanges can engage the tissue walls such that the flange ends do not migrate or move. The double walled flanges can hold the opposing tissue planes in place. The flanges can engage the tissue walls to control the positioning of the tissue walls and hold the tissue in a desired orientation to the tissue engaged by the other end of the stent.

The stents disclosed herein have additional strength over prior art stent designs. The double walled flange structure and cuff on the stent provide additional strength for the stent to engage the opposing tissue planes. The expanded double-walled flange can form an angle of about 90 degrees with the saddle region. The cuff at each end of the stent provides additional strength for the flange to engage the tissue walls.

The stent can be formed from woven shaped memory metal wires, such as nitinol or eligiloy. The wires can have a relatively small diameter, typically in the range from 0.001 inch to 0.02 inch, usually from 0.002 inch to 0.01 inch, where the braid will include from as few as 10 to as many as 200 wires, more commonly being from 20 wires to 100 wires. In exemplary cases, the wires will be round having diameters in the range from 0.003 inch to 0.007 inch with a total of from 24 to 60 wires. The wires are braided into a tubular geometry by conventional techniques, and the tubular geometry will be heat-treated to impart the desired shape memory. Usually, the braided tube will be formed into the desired final (deployed) configuration with the flanges at each end. Such a flanged configuration will then be heat set or formed into the braid so that, in the absence of a radially constraining or axially elongating force, the anchor will assume the foreshortened configuration with the flanges at each end. Such foreshortened-memory configurations will allow the anchor to be delivered in a constrained configuration (either radially or axially elongated) and thereafter released from constraint so that the body assumes the flanged configuration at the target site. The woven stent design can promote delivery with its flexibility, collapsibility, and elasticity.

Figure 22B:
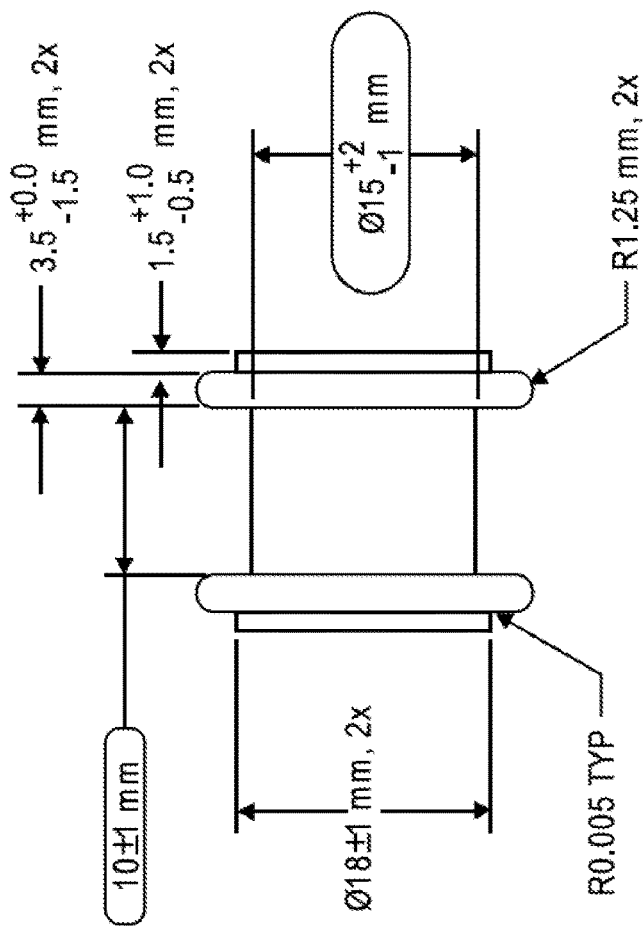
FIGS. 22A-22B is a drawing with dimensions of a stent in accordance with an embodiment.
Figure 22A:
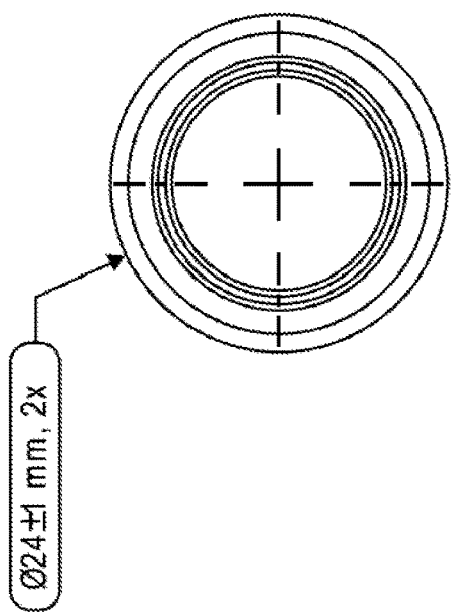

Expanded stent shapes and sizes can be manufactured with controlled dimensions, such as the internal diameter and length for the central saddle region and diameter of the double walled flanges. A stent (illustrated in detail in FIGS. 22A and 22B) with a 15 mm internal diameter of the saddle region (illustrated as d in FIG. 19) with a 10 mm saddle length (illustrated as L in FIG. 19) and 24 mm flange diameter (illustrated as D in FIG. 19) can be used. The stent structures are illustrated in detail in FIG. 22A (cross-section) and 22B (side-view). FIG. 22B illustrates a cuff or lip diameter of 18 mm.

A stent with a 10 mm internal diameter of the saddle region with a 10 mm saddle length and 21 mm flange diameter can be used. A stent with a 6 mm internal diameter of the saddle region with an 8 mm saddle length and 15 mm flange diameter can be used. A stent with an 8 mm internal diameter of the saddle region with an 8 mm saddle length and 17 mm flange diameter can be used. A stent with a 10 mm internal diameter of the saddle region with a 6 mm saddle length and 21 mm flange diameter can be used.

The stents or tissue anchors can be adapted to be delivered by a catheter based delivery device, such as the delivery device disclosed herein, typically an endoscopic delivery catheter. The catheter can have a small diameter in the range from 1 mm to 8 mm, usually from 2 mm to 5 mm. Thus, the elongated tubular configuration of the anchor body will usually have a diameter less than that of the catheter diameter, usually from 0.8 mm to 7.5 mm, more usually from 0.8 mm to 4.5 mm, where the double-walled flanged structures will be expandable significantly, usually being in the range from 3 mm to 70 mm, more usually in the range from 5 mm to 40 mm. The cylindrical saddle region of the anchor will often not increase in diameter during deployment, but may optionally increase to a diameter from 2 mm to 50 mm, more usually from 5 mm to 20 mm. When present, the lumen or passage through the deployed tissue anchor can have a variety of diameters, typically from as small as 0.2 mm to as large as 40 mm, more usually being in the range from 1 mm to 20 mm, and typically having a diameter which is slightly smaller than the expanded diameter of the cylindrical saddle region. The length of the body may also vary significantly. Typically, when in the elongated tubular configuration, the body will have a length in the range from 7 mm to 100 mm, usually from 12 mm to 70 mm. When deployed, the body will be foreshortened, typically by at least 20%, more typically by at least 40% and often by 70% or greater. Thus, the foreshortened length will typically be in the range from 2 mm to 80 mm, usually in the range from 2.5 mm to 60 mm, and more usually being in the range from 3 mm to 40 mm.

In some embodiments the body of the tissue anchor may consist of the woven filament braid with no other coverings or layers. In some embodiments the tissue anchor may further comprise a membrane or other covering formed over at least a portion of the body. The membrane can be used to prevent or inhibit tissue ingrowth to allow the device to be removed after having been implanted for weeks, months, or longer. Suitable membrane materials include polytetrafluoroethylene (PTFE), expanded PTFE (ePTFE), silicone, polypropylene, urethane polyether block amides (PEBA), polyethyleneterephthalate (PET), polyethylene, C-Flex™ thermoplastic elastomer, Krator™, SEBS and SBS polymers, and the like.

In some embodiments the membranes may be formed over the entire portion of the anchor or stent. In some embodiments the membrane or covering is formed over only a portion of the anchor or stent. The covering or membrane may be formed over the exterior or interior of the body and will typically be elastomeric so that the membrane conforms to the body in both the elongated and foreshortened configurations.

The stents can be coated with active compounds, such as therapeutic compounds to provide therapy to the tissue areas adjacent to the stent. In some embodiments the therapeutic compounds can be used to reduce tissue attachment and engagement with the stent during tissue healing after the deployment of the stent. Coatings and surfaces that do not promote tissue in-growth can be used in some embodiments. For example, Sirolimus and its analogs can be used to halt cell proliferation. Taxols can also be used to halt cell proliferation, in addition to being used in cancer treatment. Silicone and other surfaces can be used to stop or slow the rate of cell proliferation and in-growth.

In some embodiments the therapeutic compounds can promote healing of the tissue and formation of a healthy anastomosis. The therapeutic compound can be a medicine that is released from the stent over a period of time. In some embodiments the therapeutic compound can be used to treat tissue or anatomy adjacent to the stent location. In some embodiments the therapeutic agent can be used with a stent that is not fully covered to promote tissue in-growth. For example, a titanium oxide layer or coating can be used to promote cell proliferation and tissue in-growth. Biologic compounds such as cytokines and hormones can promote tissue growth as well.

The number, size, shape, and configuration of the wires along with the expanded shape of the stent (e.g. sizes of the flanges, cuffs, and saddle) can be selected to achieve an expanded stent with a desired properties. The strength of the double-walled flanged structures will depend on the number, size, stiffness, and weave pattern(s) of the individual wires used to form the tubular anchor body. For example, a design with a large number of nitinol wires, for example 48, but a relatively small wire diameter, for example 0.006 inches, will form a braid structure with a saddle region which remains flexible and double-walled flanges which are relatively film. Use of fewer wires, for example 16, and a larger wire diameter, for example 0.016 inches, will form a braid structure with a relatively rigid saddle region and relatively stiff, non-flexible flanges. Usually, the more flexible design is desirable.

In some embodiments, it is preferred that the double-walled flange structures have a preselected bending stiffness in the range from 1 g/mm to 100 g/mm, preferably in the range from 4 g/mm to 40 g/mm. Similarly, it is preferred that the central saddle region have a preselected bending stiffness in the range from 1 g/mm to 100 g/mm, preferably from 10 g/mm to 100 g/mm.

The bending stiffness of the flange can be determined by the following test. The distal flange is secured in a fixture. The outer diameter of the flange is pulled in a direction parallel to the axis of the tissue anchor using a hook attached to a Chatillon force gage. The saddle of anchor is held in a hole in a fixture and force (grams) and deflection (mm) are measured and recorded. The bending stiffness of the flange can be determined by the following test. The distal flange is secured in a fixture. The outer diameter of the flange is pulled in a direction perpendicular to axis of the tissue anchor using a hook attached to a Chatillon force gage. The saddle of anchor is held in a hole in a fixture and force (grams) and deflection (mm) are measured and recorded.

The pull out strength of the stent can be measured. Upper and lower test fixtures are assembled from a silicon sheet having a set orifice size. The orifice size corresponds to the stent saddle diameter. A force gauge can be mounted to one of the test fixtures with the other fixture attached to a Chatillon test stand. The upper and lower test fixtures are aligned next to each other and a tube can be used to deploy the proximal and distal flanges of the stent on opposing sides of the silicone sheets on the upper and lower test fixtures. The Chatillon test stand speed is set and the force gauge is zeroed. Next, the stent is pulled until either flange slips through the respective orifice. The force required to pull the stent flange through the orifice is recorded for the tested stent.

Stent pull out strength tests were performed using commercially available stent designs and the designs disclosed herein. Solus™ 10 French double pigtail stents from Cook Medical were tested with pull out strengths ranging from 98 grams (force) to 183 grams. Advanix™ 10 French double pigtail stents from Boston Scientific were tested with pull out strengths ranging from 162 grams to 380 grams. Cook Zimmon™ 7 French double pigtail stents were tested with pull out strengths ranging from 200 grams to 217 grams. Xlumena stents with a double walled flange structure and a saddle diameter of 10 mm were tested with pull out strengths ranging from 338 grams to 600 grams. The Xlumena stents showed improved pull out strengths over the tested prior art double pig tail stents along with improved fluid communication between the body lumens.

In some embodiments a stent is deployed with a pull out strength of greater than about 400 grams. In some embodiments a stent is deployed with a pull out strength of greater than about 500 grams. In some embodiments a stent is deployed with a pull out strength of greater than about 600 grams.

A cylindrical saddle region remains on the anchor body between the deployed flanges, where the flanges are able to press against the tissue layers to provide the approximating force. Typically, the body will be foreshortened to a degree selected to apply sufficient pressure to the tissues to hold them together without causing significant tissue injury or necrosis. Usually, the applied pressure will be in the range from 0.005 $g/mm^2$ to 5 $g/mm^2$, usually from 0.2 $g/mm^2$ to 1 $g/mm^2$.

As used herein "about", "substantially", "generally", and other relative terms refer to approximately or reasonably close to. In some cases the relative terms can refer to plus or minus 10%. In some cases the relative terms can refer to plus or minus 5%. In some cases the relative terms can refer to plus or minus 2%. In some cases the relative terms can refer to plus or minus 1%.

Although the foregoing invention has been described in some detail by way of illustration and example, for purposes of clarity of understanding, it will be obvious that various alternatives, modifications and equivalents may be used and the above description should not be taken as limiting in scope of the invention which is defined in part by the appended claims.

The invention claimed is:

1. A catheter assembly, comprising:
   an outer sheath having a lumen extending therethrough along a longitudinal axis of the assembly;
   an inner body having a proximal end, a distal end, and a passage extending therethrough along the longitudinal axis, a portion of the inner body receivable within the lumen of the outer sheath;
   a tip positioned proximate the distal end of the inner body, the tip being conically shaped and having a conductive portion including a distal ring-shaped cutting feature disposed on a distal-most face of the tip and a proximal cutting feature extending proximally from the distal ring-shaped feature to a maximum radial position, the maximum radial position defining a vertical length between the maximum radial position and the longitudinal axis, wherein the length is less than 50% of a maximum outer diameter of the outer sheath; and
   a stent constrained on the inner body.

2. The catheter assembly of claim 1, wherein the inner body is configured to accept a guidewire receivable within the passage of the inner body.

3. The catheter assembly of claim 1, wherein the tip comprises an insulating portion.

4. The catheter assembly of claim 3, wherein a position along the insulating portion extends radially outward from the longitudinal axis further than the maximum radial position.

5. The catheter assembly of claim 3, wherein the insulating portion comprises an insulating sleeve, or an insulating collar, or both.

6. The catheter assembly of claim 3, wherein an edge of the insulating portion coincides with the maximum radial position of the conductive portion.

7. The catheter assembly of claim 3, wherein the conductive portion comprises a material, and wherein the material includes a portion that extends proximally beyond the maximum radial position and is encompassed by the insulating portion.

8. The catheter assembly of claim 1, wherein the stent is releasably constrained in an undeployed configuration between the outer sheath and the inner body.

9. The catheter assembly of claim 8, wherein the stent is configured to self-expand from the undeployed configuration to a deployed configuration when released from between the outer sheath and the inner body.

10. The catheter assembly of claim 9, wherein the stent forms distal and proximal flanges in the deployed configuration.

11. The catheter assembly of claim 1, wherein the conductive portion is configured to be electrically coupled to an electrosurgical generator, the generator configured to supply about 50 watts to about 100 watts of power to the conductive portion of the tip.

12. A catheter assembly, comprising: an outer sheath having a lumen extending therethrough; an inner body having a proximal end, a distal end, and a passage extending therethrough, a portion of the inner body receivable within the lumen of the outer sheath; a tip positioned near the distal end of the inner body, the tip being conically shaped and having an insulating portion and a conductive portion, the conductive portion comprising a distal cutting portion disposed on a distal-most face of the tip and a proximal cutting portion extending radially outwardly and proximally from the distal cutting portion on the distal-most face to a maximum diameter conductive position of the catheter assembly, a position along the insulating portion, the outer sheath, or both extending radially outward further than the maximum diameter conductive position of the conductive portion, the conductive portion configured to be electrically coupled to an electrosurgical generator, the maximum diameter conductive position less than or equal to one half of a diameter of the outer sheath; and a stent constrained on the inner body.

13. The catheter assembly of claim 12, wherein the stent is releasably constrained in an undeployed configuration between the outer sheath and the inner body.

14. The catheter assembly of claim 13, wherein the stent is configured to self-expand from the undeployed configuration to a deployed configuration when released from between the outer sheath and the inner body.

15. A catheter assembly, comprising:
   an outer sheath having a lumen extending therethrough along a longitudinal axis of the assembly;
   an inner body having a proximal end, a distal end, and a passage extending therethrough along the longitudinal axis, a portion of the inner body receivable within the lumen of the outer sheath; and
   a tip positioned near the distal end of the inner body, the tip being conically shaped and having a conductive portion, the conductive portion including a plane transverse to the longitudinal axis at the distal end of the inner body that defines a ring-shaped cutting feature on a distal-most face of the tip, the conductive portion further defines a proximal cutting portion extending from the ring-shaped cutting feature proximally and radially outward from the longitudinal axis to a maximum radial position, the maximum radial position defining a vertical length between the maximum radial position and the longitudinal axis that is less than 50% of a maximum outer diameter of the outer sheath, the conductive portion configured to be electrically coupled to an electrosurgical generator; and
   a stent constrained on the inner body.

16. The catheter assembly of claim 15, wherein the tip comprises an insulating portion.

17. The catheter assembly of claim 16, wherein the insulating portion comprises an insulating sleeve, or an insulating collar, or both.

18. The catheter assembly of claim 15, wherein the stent is releasably constrained in an undeployed configuration between the outer sheath and the inner body.

19. The catheter assembly of claim 18, wherein the stent forms distal and proximal flanges in a deployed configuration.

* * * * *